(12) United States Patent
Wei et al.

(10) Patent No.: US 8,425,896 B2
(45) Date of Patent: *Apr. 23, 2013

(54) TREATMENT OF TUMORS WITH RECOMBINANT INTERFERON ALPHA

(75) Inventors: Guangwen Wei, Chengdu (CN); Rongbing Guo, Chengdu (CN); Renhuai Zhang, Chengdu (CN)

(73) Assignee: Sichuan Biotechnology Research Center, Chengdu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/019,044

(22) Filed: Feb. 1, 2011

(65) Prior Publication Data

US 2011/0189128 A1 Aug. 4, 2011

Related U.S. Application Data

(63) Continuation of application No. 12/105,455, filed on Apr. 18, 2008, now Pat. No. 8,114,395, which is a continuation of application No. 10/650,365, filed on Aug. 28, 2003, now Pat. No. 7,364,724, which is a continuation-in-part of application No. PCT/CN02/00128, filed on Feb. 28, 2002.

(30) Foreign Application Priority Data

Feb. 28, 2001 (CN) ..................................... 1104367

(51) Int. Cl.
*A61K 38/21* (2006.01)
*A61K 38/00* (2006.01)
*C07K 14/56* (2006.01)

(52) U.S. Cl.
USPC ............................ 424/85.7; 530/351; 514/1.1

(58) Field of Classification Search ........................ None
See application file for complete search history.

(56) References Cited

U.S. PATENT DOCUMENTS

| | | | |
|---|---|---|---|
| 4,179,337 A | 12/1979 | Davis et al. | |
| 4,462,940 A | 7/1984 | Hanisch et al. | |
| 4,672,108 A | 6/1987 | Kung et al. | |
| 4,681,930 A | 7/1987 | Kung et al. | |
| 4,695,623 A | 9/1987 | Stabinsky | |
| 4,897,471 A | 1/1990 | Stabinsky | |
| 5,372,808 A | 12/1994 | Blatt et al. | |
| 5,441,734 A | 8/1995 | Reichert et al. | |
| 5,602,232 A | 2/1997 | Reichert et al. | |
| 5,710,027 A | 1/1998 | Hauptmann et al. | |
| 5,874,304 A | 2/1999 | Zolotukhin et al. | |
| 5,972,331 A | 10/1999 | Reichert et al. | |
| 5,980,884 A | 11/1999 | Blatt et al. | |
| 6,087,478 A | 7/2000 | Vinkemeier et al. | |
| 6,114,145 A | 9/2000 | Olsen et al. | |
| 6,532,437 B1 | 3/2003 | Clardy et al. | |
| 6,546,074 B1 | 4/2003 | Blundell et al. | |
| 6,579,695 B1 | 6/2003 | Lambalot et al. | |
| 7,364,724 B2 | 4/2008 | Wei et al. | |
| 2002/0043262 A1 | 4/2002 | Langford et al. | |
| 2004/0115169 A1 | 6/2004 | Wolfe et al. | |
| 2004/0202641 A1 | 10/2004 | Wei et al. | |

FOREIGN PATENT DOCUMENTS

| | | |
|---|---|---|
| AU | 2003248419 | 11/2003 |
| CN | 1099799 A | 3/1995 |
| CN | 1120846 A | 4/1996 |
| CN | 1186120 A | 7/1998 |
| CN | 1217660 A | 5/1999 |
| CN | 1256148 A | 6/2000 |
| CN | 1062565 C | 2/2001 |
| CN | 1291198 A | 4/2001 |
| CN | 1375502 A | 10/2002 |
| CN | 1384116 A | 12/2002 |
| CN | 1098103 C | 1/2003 |
| CN | 1478545 A | 3/2004 |
| DE | 4329756 | 3/1995 |
| EP | 0083734 B1 | 12/1982 |
| EP | 422697 A | 4/1991 |
| EP | 0777495 B1 | 10/1995 |
| EP | 0736303 B1 | 10/1996 |
| WO | WO 83/04053 | 11/1983 |
| WO | WO 93/21229 | 10/1993 |
| WO | WO 94/19373 | 9/1994 |
| WO | WO 97/13845 | 4/1997 |
| WO | WO 97/27866 | 8/1997 |
| WO | WO 99/40117 | 8/1999 |
| WO | WO 01/35987 A1 | 5/2001 |
| WO | WO 02/36627 | 5/2002 |
| WO | WO 02/080958 | 10/2002 |
| WO | WO 2005/021777 A2 | 3/2005 |
| WO | WO 2005/034853 A2 | 4/2005 |
| WO | WO 2005/067963 | 7/2005 |
| WO | WO 2006/134497 | 12/2006 |

OTHER PUBLICATIONS

European Search Report for Huiyangtech (USA), Inc., Apr. 26, 2011, Application No. EP 10 19 3126.

European Supplemental Search Report for Huiyangtech (USA), Inc., Application No. EP 04809634.1, Filed Mar. 26, 2006, Dated Jun. 17, 2008, Date of Completing of the Search: Jun. 10, 2008.

Notification of Transmittal of International Preliminary Report on Patentability (Chapter II of the Patent Cooperation Treaty) for PCT/US04/28067 for Huiyangtech (USA), Inc., Dated Mar. 5, 2007.

(Continued)

*Primary Examiner* — Robert Landsman
*Assistant Examiner* — Bruce D Hissong
(74) *Attorney, Agent, or Firm* — Law Offices of Albert Wai-Kit Chan, PLLC

(57) ABSTRACT

This invention provides a recombinant super-compound interferon or an equivalent thereof with changed spatial configuration. The super-compound interferon possesses antiviral or anti-tumor activity and therefore is useful to prevent and treat viral diseases and cancers. This invention also provides an artificial gene which codes for the super-compound interferon or its equivalent. Finally, this invention provides methods to produce recombinant super-compound interferon or its equivalent and various uses of said interferon.

14 Claims, 9 Drawing Sheets

OTHER PUBLICATIONS

Figure 3:
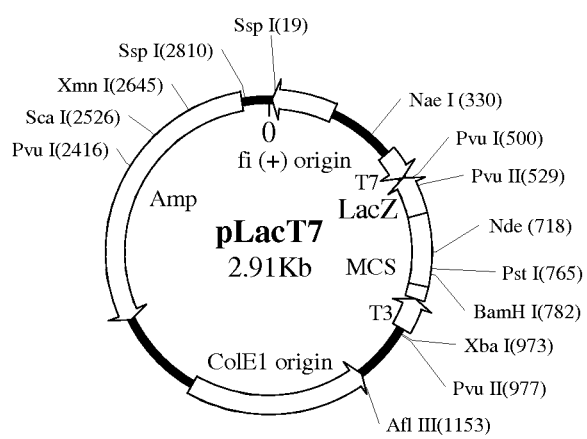

Indian Examiner's Report, May 7, 2009, Indian Application No. 00311/MUMNP/2006, Huiyangtech (USA) Inc., Filed Mar. 24, 2006.
U.S. Office Action, Jul. 18, 2008, Guangwen Wei, U.S. Appl. No. 11/817,926, filed Sep. 6, 2007.
Gao Zhan-Cheng et al., 2003, "Clinical investigation of outbreak of nosocomial severe acute respiratory syndrome", Database Medline, Database accession No. NLM12837162.
Christine A. Biron, 2001, "Interferons α and β as Immune Regulators—A New Look," Immunity,14: 661-664.
David Goldstein and John Laszlo, 1988, "The Role of Interferon in Cancer Therapy: A Current Perspective", CA Cancer J Clin., 38:258-277.
Huang, K.J. et al., Feb. 2005, "An interferon-gamma-related cytokine storm in SARS patients," J. Med. Virol. 75(2): 185-94. [Abstract only].
Loutfy et al., 2003, "Interferon Alfacon-1 Plus Corticosteroids in Severe Acute Respiratory Syndrome—A preliminary Study", JAMA 290(24):3222-3228.
Spada S., 2004, "Infergen", Directory of Approved Biopharmaceutic. Prod., 116-117.
Canadian Office Action, May 10, 2011, Huiyangtech (USA), Inc, Canadian Application No. 2,535,982, Filed Feb. 15, 2006, corresponding to Int'l App'l No. PCT/US2004/028067, Filed Aug. 26, 2004.
U.S. Office Action, Jun. 20, 2011, Guangwen Wei, U.S. Appl. No. 12/246,153, filed Oct. 6, 2008.
U.S. Office Action, Jun. 20, 2011, Guangwen Wei, U.S. Appl. No. 12/105,455, filed Apr. 18, 2008.
U.S. Office Action, Jan. 25, 2011, Guangwen Wei, U.S. Appl. No. 10/928,474, filed Aug. 26, 2004.
U.S. Office Action, Jun. 14, 2011, Guangwen Wei, U.S. Appl. No. 12/554,297, filed Sep. 4, 2009.
International Search Report, Application No. PCT/CN02/00128 for Sichuan Biotechnology Research Center, "Recombination Super Compound Interferon Used as Hepatitis B Surface Antigen and E Antigen Inhibitor," Filed Feb. 28, 2002, Dated Aug. 8, 2002, Date of Completion of the Search: Jul. 23, 2002.
International Preliminary Examination Report, Application No. PCT/CN02/00128 for Sichuan Biotechnology Research Center, "Recombination Super Compound Interferon Used as Hepatitis B Surface Antigen and E Antigen Inhibitor," Filed Feb. 28, 2002, Dated Feb. 15, 2004.
Supplementary European Search Report for Sichuan Biotechnology Research Center, Application No. EP 02702211, Filed Feb. 28, 2002, Date of Completing of the Search: Feb. 23, 2005.
International Search Report, Application No. PCT/US04/28068 for Huiyangtech (USA) Inc., Filed Aug. 26, 2004, Dated Mar. 4, 2005.
Written Opinion for Huiyangtech (USA) Inc., International Searching Authority for PCT/US04/28068, Filed Aug. 26, 2004, Dated Mar. 4, 2005.
PCT Notification of Transmittal of International Preliminary Report on Patentability for Huiyangtech (USA) Inc., International Application No. PCT/US04/28068, Filed Aug. 26, 2004, Dated May 13, 2005.
International Search Report, Application No. PCT/US2004/028067 for Huiyangtech, Inc., "Uses of interferons with altered spatial structure," Filed Aug. 26, 2004, Dated Feb. 27, 2006, Date of Completion of the Search: Nov. 2, 2005.
Written Opinion of the International Searching Authority for PCT/US2004/028067, Dated Aug. 26, 2004 for Huiyangtech (USA) Inc., Dated Nov. 2, 2005.
Notification of Transmittal of the International Search Report and the Written Opinion of the International Searching Authority for Guangwen Wei (International Search Report and Written Opinion included), Application No. PCT/IB2006/002340, Filed Mar. 9, 2006, Dated May 10, 2007.
Notification Concerning Transmittal of International Preliminary Report on Patentability (Chapter I of the Patent Cooperation Treaty) for PCT/IB2006/002340 for Guangwen Wei, Dated Sep. 20, 2007.
Written Opinion of the Australian Patent Office for SG 200601209-0, National Phase under Chapter II Based on PCT/US2004/028067 for Huiyangtech (USA) Inc., Dated Dec. 4, 2007.
Amato, Ivan, Jan. 22, 2007, "Silent No Longer: Researchers Unearth another Stratum of Meaning in the Genetic Code," Chemical and Engineering News, 85(4):38-40.
Apeler, H. et al., Aug. 1, 1997, "Expression of Natural and Synthetic Genes Encoding Herpes Simplex Virus 1 Protease in *Escherichia coli* and Purification of the Protein," European Journal of Biochemistry, 247 (3):890-895, XP002318941, Issn: 0014-2956.
Ausubel et al., Eds., 1999, Chapter Ten, "Analysis of Proteins," from Short Protocols in Molecular Biology, 4th ed., p. 10-1 to 10-8.
Cao, Hongpeng, and Tao, Peizhen, "Effect of Anti-HBV of 6 Drugs Include Lamividine," Natl. Med. J. China, 2001, 81(16):1004-1007.
Cinatl et al., 2003, "Treatment of SARS with Human Interferons," The Lancet, 362:293-294.
Day et al., 1992, "Engineered Disulfide Bond Greatly Increases Specific Activity of Recombinant Murine Interferon-Beta," Journal of Interferon Res., 12:139-143.
Duan et al., 2003, "Anti-SARS virus activities of different recombinant human interferons in cell culture system," Chinese J. Clin. Virol., 17(3):205-208.
Fei et al., 1999, "Clinical Observation of Effect on Treatment of Chronic Hepatitis B by a Combination of Interferon and Lamividine," Shandong Medical Journal, 39(11):3-4.
Gao et al., 1999, "Treatment of Hepatitis Virus Related Pediatric Nephritis With IFN," Academic Journal of Jinlin Hospital, 12(1):155-157.
Guzman, Luz-Maria et al, 1995, "Tight Regulation, Modulation, and High-Level Expression by Vectors Containing the Arabinose P-Bad Promoter," Journal of Bacteriology, 177(14):4121-4130, Xp002121022, Issn: 0021-9193.
Higgins et al., 1983, "Intranasal Interferon as Protection against Experimental Respiratory Coronavirus Infection in Volunteers," Antimicrobial Agents and Chemotherapy 24(5):713-715.
Holland, C.C. and T.L. Wright, "New approaches to treatment of chronic viral hepatitis," Pathology (Phila.), 1994: 3(1), Full Article.
Huang, Wanzhi et al., Jun. 72, 2000, "Use of the Arabinose pBAD Promoter for Tightly Regulated Display of Proteins on Bacteriophage," Gene (Amsterdam), 251(2):187-197, XP004206676, Issn: 0378-1119.
Lei et al., 1995, "Observation on Clinical Treatment of Chronic Hepatitis B by Purified Human Leucocyte Interferon," Chinese Journal of Practical Internal Medicine, 15(3):155-157.
Lang et al., 2002, "Observation on Serology and Histology of Patients With Chronic Hepatitis B After Interferon Treatment," Chin. J. Infect. Dis., 20(2): 97-100.
Nackley, A.G. et al., Dec. 22, 2006, "Human Catechol-O-Methyltransferase Haplotypes Modulate Protein Expression by Altering mRNA Secondary Structure," Science, 314:1930-1932.
Nasoff et al., 1999, "High-Level Expression of Human Genes in *E. coli*," Expression, 6(2):10-11.
Pyrc, K. et al., 2007, "Antiviral strategies against human coronaviruses," Infectious Disorders—Drug Targets, (7):59-66.
Schulte-Frohlinde, et al., Feb. 21, 2002, "Different Activities of Type I interferons on Hepatitis B virus core promoter regulated transcription," Cytokine, 17(4): 214-220.
Wang, Xiangye, and Li, Xuegang, 1994, "Comparing Effect of Three Drugs on Turning HBEAG to Negative," Qienwei Medical Journal, 11(4):197-198.
Yasuda, et al., 2000, "Spectrum of virus inhibition by consensus interferon YM643." Antiviral Chemistry & Chemotherapy, 11:337-341.
Wu, et al., 2003, "A hospital outbreak of severe acute respiratory syndrome in Guangzhou, China." Chinese Medicine Journal, 116(6):811-818.
Zhao, Z. et al., 2003, "Description and clinical treatment of an early outbreak of severe acute respiratory syndrome (SARS) in Guangzhou, PR China," Journal of Med. Microbiol. 52:715-720.
Australian Examiner's Report for Sichuan Biotechnology Research Center, Australian Application No. 2003248419, Filed Sep. 26, 2003, Dated Dec. 12, 2005.

Australian Examiner's Report for Sichuan Biotechnology Research Center, Australian Application No. 2003248419, Filed Sep. 26, 2003, Dated Jun. 1, 2006.
Australian Notice of Acceptance for Sichuan Biotechnology Research Center, Australian Application No. 2003248419, Filed Sep. 26, 2003, Dated Dec. 18, 2006.
European Communication for Sichuan Biotechnology Research Center, European Application No. 02702211.0, Filed Sep. 25, 2003, Dated Dec. 14, 2006.
Examiner's Report for Wei et al., European App'l No. 02702211.0, Filed Sep. 25, 2003, Dated Dec. 13, 2007.
Indian Examination Report for Sichuan Biotechnology Research Center, Indian Application No. 279/MUM/2004, Filed Mar. 5, 2004, Dated Aug. 2, 2007.
Malaysian Examiner's Report for Sichuan Biotechnology Research Center, Malaysian Application No. PI 20033246, Filed Aug. 28, 2003, Dated Mar. 8, 2007.
Singapore Written Opinion for Huiyangtech (USA), Inc., Singapore Application No. 200601204-1, Filed Feb. 23, 2006, Dated Jul. 19, 2007.
Examiner's Written Opinion for Huiyangtech (USA), Inc., Singaporean App'l No. 200601209-0, Filed Feb. 23, 2006, Dated Jan. 8, 2008.
Taiwanese Office Action for Sichuan Biotechnology Research Center, Taiwanese Application No. 92,123,846, Filed Aug. 28, 2003, Dated Sep. 21, 2006.
Taiwanese Formal Rejection for Sichuan Biotechnology Research Center, Taiwanese Application No. 92,123,846, Filed Aug. 28, 2003, Dated Dec. 29, 2006.
Notice of Allowance and Fee(s) Due notice for Wei et al., U.S. Appl. No. 10/650,365, filed Aug. 28, 2003, dated Jul. 26, 2007.
U.S. Office Action for Wei et al., U.S. Appl. No. 10/650,365, filed Aug. 28, 2003, Dated Aug. 23, 2005.
U.S. Office Action for Wei et al., U.S. Appl. No. 10/650,365, filed Aug. 28, 2003, Dated Sep. 20, 2006.
U.S. Office Action for Wei et al., U.S. Appl. No. 10/650,365, filed Aug. 28, 2003, Dated Mar. 7, 2007.
U.S. Office Action for Guangwen Wei, U.S. Appl. No. 10/927,975, filed Aug. 26, 2004, Dated Apr. 3, 2007.
U.S. Office Action for Guangwen Wei, U.S. Appl. No. 10/928,956, Filed Aug. 26, 2004, Dated Jun. 14, 2007.
U.S. Office Action for Guangwen Wei, U.S. Appl. No. 10/928,956, Filed Aug. 26, 2004, Dated Dec. 15, 2006.
Advisory Action Before the Filing of an Appeal Brief for Guangwen Wei, U.S. Appl. No. 10/928,474, Filed Aug. 26, 2004, Dated May 22, 2007.
U.S. Office Action for Guangwen Wei, U.S. Appl. No. 10/928,474, Filed Aug. 26, 2004, Dated Aug. 9, 2007.
U.S. Office Action for Guangwen Wei, U.S. Appl. No. 10/928,474, Filed Aug. 26, 2004, Dated Feb. 9, 2007.
U.S. Office Action for Guangwen Wei, U.S. Appl. No. 10/928,474, Filed Aug. 26, 2004, Dated Aug. 22, 2006.
U.S. Office Action for Guangwen Wei, U.S. Appl. No. 11/077,813, Filed Mar. 10, 2005, Dated Aug. 1, 2007.
U.S. Office Action for Guangwen Wei, U.S. Appl. No. 11/077,813, Filed Mar. 10, 2005, Dated Nov. 27, 2006.
U.S. Office Action for Guangwen Wei, U.S. Appl. No. 11/077,813, Filed Mar. 10, 2005, Dated Aug. 8, 2006.
U.S. Office Action for Wei et al., U.S. Appl. No. 10/650,365, Filed Aug. 28, 2003, Dated Mar. 20, 2006.
U.S. Office Action for Guangwen Wei, U.S. Appl. No. 10/927,975, filed Aug. 26, 2004, Dated Sep. 19, 2007.
Notice of Allowance for Wei et al., U.S. Appl. No. 10/928,956, filed Aug. 26, 2004, Dated Apr. 2, 2008.
U.S. Office Action for Guangwen Wei, U.S. Appl. No. 10/928,474, filed Aug. 26, 2004, Dated Jan. 4, 2008.
Notice of Allowance for Wei et al., U.S. Appl. No. 10/650,365, filed Aug. 28, 2003, Dated Dec. 12, 2007.
Advisory Action before the Filing of an Appeal Brief, U.S. Appl. No. 10/928,474, filed Aug. 28, 2003, Dated Mar. 18, 2008.
U.S. Office Action for Guangwen Wei, U.S. Appl. No. 10/927,975, filed Aug. 26, 2004, Dated Apr. 2, 2008.

U.S. Office Action for Guangwen Wei, U.S. Appl. No. 11/077,813, filed Mar. 10, 2005, Dated Feb. 6, 2008.
Indian patent for 279/MUM/2004, Jan. 28, 2009, Sichuan Biological Research Center.
Singapore grant for 200601204-1, Mar. 31, 2009, Huiyangtech(USA), Inc.
Singapore grant for 200304969, Nov. 30, 2005, Sichuan Biological Research Center.
Canadian Office Action, Apr. 21, 2008, for Sichuan Biotechnolgy Research Center, Canadian Application No. 2,439,503, Filed Aug. 27, 2003.
Chinese First Notification of Examination, Apr. 18, 2003, for Sichuan Biological Research Center, Chinese Application No. 01104367.9, Filed Feb. 28, 2001. [with full English translation].
Chinese Second Notification of Examination, Oct. 17, 2003, for Sichuan Biological Research Center, Chinese Application No. 01104367.9, Filed Feb. 28, 2001. [with full English translation].
Chinese Third Notification of Examination, Jan. 2, 2004, for Sichuan Biological Research Center, Chinese Application No. 01104367.9, Filed Feb. 28, 2001. [with full English translation].
Chinese Fourth Notification of Examination, Jun. 4, 2004, for Sichuan Biological Research Center, Chinese Application No. 01104367.9, Filed Feb. 28, 2001. [with full English translation].
Chinese Decision About Rejection, Nov. 12, 2004, for Sichuan Biological Research Center, Chinese Application No. 01104367.9, Filed Feb. 28, 2001. [with full English translation].
Chinese Decision About the Reexamination, Oct. 26, 2005, for Sichuan Biological Research Center, Chinese Application No. 01104367.9, Filed Feb. 28, 2001. [with full English translation].
Chinese Notification of Patent for Invention, Oct. 26, 2005, for Sichuan Biological Research Center, Chinese Application No. 01104367.9, Filed Feb. 28, 2001. [with full English translation].
Chinese First Office Action, Mar. 27, 2009, for Huiyangtech (USA), Inc., Chinese Application No. 200480031910.0, Filed Apr. 28, 2006.
Chinese First Office Action, Feb. 20, 2009, for Huiyangtech (USA), Inc., Chinese Application No. 200480031909.8, Filed Apr. 28, 2006.
Chinese First Office Action, May 22, 2009, for Guangwen Wei, Chinese Application No. 200680007733.1, Filed Sep. 10, 2007.
European Communication, Jun. 19, 2006, for Sichuan Biological Research Center, European Application No. 02702211.0, Filed Mar. 23, 2006.
European Communication, Aug. 26, 2008, for Sichuan Biological Research Center, European Application No. 02702211.0, Filed Mar. 23, 2006.
European Communication, Nov. 28, 2008, for Huiyangtech (USA), Inc., European Application No. EP 04809634.1, Filed Mar. 23, 2006.
European Communication, Nov. 27, 2008, for Huiyangtech (USA), Inc., European Application No. EP 04782529.4, Filed Mar. 23, 2006.
Indian Office Action, Oct. 24, 2008, for Sichuan Biological Research Center, Indian Patent Application No. 280/MUM/2004, Filed Mar. 5, 2004.
Indian Examination Report, Aug. 1, 2008, for Huiyangtech(USA), Inc., Indian Application No. 310/MUMNP/2006, Filed Oct. 3, 2006.
Japanese Notification of Reasons of Refusal, Jun. 17, 2008, for Sichuan Biotechnology Research Center, Japanese Application No. 2002-578997, Filed Aug. 28, 2003. [with full English translation].
Malaysian Office Action, Aug. 11, 2008, for Sichuan Biological Research Center, Malaysian Patent Application No. PI 20033246, Filed Aug. 28, 2003.
Malaysian Office Action, Jan. 16, 2009, for Sichuan Biological Research Center, Malaysian Patent Application No. PI 20033246, Filed Aug. 28, 2003.
Singapore Written Opinion, Apr. 29, 2008, for Huiyangtech (USA), Inc., Singapore Application No. 200601204-1, Filed Feb. 23, 2006.
Taiwanese Formal Rejection, Dec. 11, 2006, for Sichuan Biotechnology Research Center, Taiwanese Application No. 92,123,846, Filed Aug. 28, 2003. [with full English translation].
Taiwanese Examination Report, Dec. 12, 2008, for Guangwen Wei, Taiwanese Application No. 95107930, Filed Mar. 9, 2006. [with full English translation].
U.S. Office Action, Apr. 29, 2005, for Guangwen Wei, U.S. Appl. No. 10/650,365, Patent No. 7,364,724, filed Aug. 28, 2003.

U.S. Office Action, Aug. 8, 2006, for Guangwen Wei, U.S. Appl. No. 10/928,956, filed Aug. 26, 2004.
U.S. Notice of Allowance and Fee(s) Due, Jun. 25, 2008, for Guangwen Wei, U.S. Appl. No. 10/928,956, filed Aug. 26, 2004.
U.S. Notice of Allowance and Fee(s) Due, Sep. 22, 2008, for Guangwen Wei, U.S. Appl. No. 10/928,956, filed Aug. 26, 2004.
U.S. Examiner's Answer to Appeal Brief, Dec. 9, 2008, for Guangwen Wei, U.S. Appl. No. 10/928,474, filed Aug. 26, 2004.
U.S. Office Action, Nov. 14, 2008, for Guangwen Wei, U.S. Appl. No. 10/927,975, filed Aug. 26, 2004.
U.S. Final Office Action, Apr. 15, 2009, for Guangwen Wei, U.S. Appl. No. 10/927,975, filed Aug. 26, 2004.
Advisory Action Before the Filing of an Appeal Brief, Jul. 17, 2008, for Guangwen Wei, U.S. Appl. No. 11/077,813, filed Mar. 10, 2005.
U.S. Office Action, Feb. 23, 2009, for Guangwen Wei, U.S. Appl. No. 11/817,926, filed Sep. 6, 2007.
Alton, K. et al., 1983, "Production, characterization and biological effects of recombinant DNA derived human IFN-α and IFN-γ analogs." In: De Maeger E, Schellekens H. eds. The Biology of Interferon System 2nd ed. Amsterdam: Elsevier Science Publishers, p. 119-128.
Blatt, L.M. et al., 1996, "The biological activity and molecular characterization of a novel synthetic interferon-alpha species, consensus interferon," Journal of Interferon and Cytokine Research, 16(7):489-499.
Heathcote, E.J.L. et al., 1998, "Re-treatment of chronic hepatitis C with consensus interferon," Hepatology 27(4):1136-1143.
Infergen (Interferon alfacon-1) Product Sheet, Amgen, Inc., Issue Date: Nov. 30, 1998.
Klein, M.L. et al., 1998, "Structural character-ization of recombinant consensus interferon-alpha," Journal of Chromatography, 454:205-215.
Ozes, O.N. et al., 1992, "A comparison of interferon-con1 with natural recombinant interferons: antiviral, antiproliferative, and natural killer-inducing activities." J. Interferon Res., 12:55-59.
Pfeffer, L.M., 1997, "Biologic activity of natural and synthetic type 1 interferons," Seminars in Oncology, 24(3 suppl. 9):S9-63-S9-69.
pBAD Expression System, "Tightly Controlled Bacterial Protein Expression," Invitrogen Corp. Publication, 2002.
Wang, C. et al., 2006, "Refolding Recombinant Human Granulocyte Colony Stimulating Factor Expressed by E. coli: A Case Study Using the Unit of Simultaneous Renaturation and Purification of Proteins," BioProcess International, 48-53.
Zeng, Zheng et al., 2000, "Transfer and expression of human interferon-α and its effect on HBV inhibition," Chinese Journal of Infectious Disease, 18(4):221-224. [English abstract only].
Austrian Written Opinion, Jun. 29, 2009, Singapore Application No. 200706014-8, Guangwen Wei, filed Mar. 9, 2006.
Canadian Office Action, Jun. 1, 2009, Sichuan Biotechnolgy Research Center, Canadian Application No. 2,439,503, Filed Aug. 27, 2003.
Chinese Examination Report, Nov. 27, 2009, Huiyangtech(USA), Inc., Chinese Application No. 200680007733.1, Filed Sep. 10, 2007.
Chinese Examination Report, Feb. 20, 2009, Huiyangtech(USA), Inc., Chinese Application No. 200480031909.8, Filed Apr. 28, 2006.
Chinese Examination Report, Nov. 20, 2009, Huiyangtech(USA), Inc., Chinese Patent Application No. 200480031910.0, Filed Apr. 28, 2006.
Chinese Examination Report, Aug. 7, 2009, Huiyangtech(USA), Inc., Chinese Application No. 200480031909.8, Filed Apr. 28, 2006.
European Communication, Jun. 19, 2009, Sichuan Biotechnology Research Center, European App'l No. 02702211.0, Filed Sep. 25, 2003.
European Examiner's Report, Jul. 29, 2009, Huiyangtech(USA), Inc., European Application No. 04782529.4, Filed Mar. 23, 2006.
European Examiner's Report, Jul. 28, 2009, Huiyangtech(USA), Inc., European Application No. 04809634.1, Filed Mar. 26, 2006.
Indian Examiner's Report, Aug. 20, 2009, Indian Application No. 00310/MUMNP/2006, Wei et al., Filed Oct. 17, 2007.
Indian Examiner's Report, Sep. 16, 2009, Indian Application No. 00311/MUMNP/2006, Huiyangtech (USA) Inc., Filed Mar. 24, 2006.
Japanese Examiner's Report, Dec. 2, 2009, Sichuan Biotechnology Research Center, Japanese Patent Application No. 2002-578997, Filed Aug. 28, 2003.
Malaysian Advisory Action, Mar. 8, 2007, Sichuan Biotechnology Research Center, Malaysian Patent Application No. PI 20033246, Filed Aug. 28, 2003.
Malaysian Office Action, Jul. 13, 2009, Guangwen Wei, Malaysian Patent Application No. PI 20061015, Filed Mar. 9, 2006.
Taiwanese Examiner's Report, May 25, 2009, Huiyangtech(USA), Inc., Taiwanese Application No. 095107930, Filed Mar. 9, 2006.
Taiwanese Examiner's Report, Mar., 2010, Huiyangtech(USA), Inc., Taiwanese App'l No. 92,123,846, Filed Aug. 28, 2003.
U.S. Office Action, Sep. 30, 2009, Guangwen Wei, U.S. Appl. No. 12/369,005, filed Feb. 11, 2009.
U.S. Office Action, Dec. 2, 2009 Guangwen Wei, U.S. Appl. No. 10/927,975, filed Aug. 26, 2004.
U.S. Office Action, Sep. 29, 2009, Guangwen Wei, U.S. Appl. No. 11/817,926, filed Mar. 9, 2005.
U.S. Office Action, Jun. 23, 2009, Guangwen Wei, U.S. Appl. No. 10/927,975, filed Aug. 26, 2004.
U.S. Office Action, Jan. 6, 2010, Guangwen Wei, U.S. Appl. No. 12/246,153, filed Oct. 6, 2008.
Greenberg et al., Sep. 2, 1976, "Effect of human leukocyte interferon on hepatitis B virus infection in patients with chronic active hepatitis", 295(10):517-522. (abstract only).
Li et al., 1999, "Antiviral effects of rhIFN-alpha 1 against seven influenza viruses", Acta. Pharmacol. Sin. 20(8):709-714.
Moore et al., 1995, "A Phase I Study of Intraperitoneal Interferon-α2b cis-Platinum plus Cyclophosphamide Chemotherapy in Patients with Untreated Stage III Epithelial Ovarian Cancer: A Gynecologic Oncology Group Pilot Study", Gynecologic Oncology, 59:267-272.
Australian Examiner's Report for Sichuan Biotechnology Research Center, Australian Application No. 2004279350 Dated Mar. 1, 2010.
U.S. Office Action, Apr. 15, 2010, for Guangwen Wei, U.S. Appl. No. 12/369,005, filed Feb. 11, 2009.
Indian Examiner's Report, May 4, 2010, Indian Application No. 00311/MUMNP/2006, Huiyangtech (USA) Inc., Filed Mar. 24, 2006.
Indian Examiner's Report, May 10, 2010, Indian Application No. 1214/MUMNP/2007, Guangwen Wei, Filed Aug. 13, 2007.
Japanese Examiner's Report, May 10, 2010, Huiyangtech (USA), Inc., Japanese Patent Application No. 2006-524916, Filed Feb. 27, 2006.
Singapore Written Opinion, Mar. 26, 2010, Guangwen Wei, Singapore Application No. 200706014-8, Filed Aug. 15, 2007.
Chinese Examination Report, Aug. 25, 2010, Huiyangtech(USA), Inc., Chinese Application No. 200680007733.1 ((With English summary), Filed Sep. 10, 2007.
Japanese Examiner's Report, Jul. 26, 2010, Huiyangtech (USA), Inc., Japanese Patent Application No. 2006-524916, Filed Feb. 27, 2006 (with English summary).
U.S. Office Action, Aug. 4, 2010, Guangwen Wei, U.S. Appl. No. 12/246,153, filed Oct. 6, 2008.
U.S. Office Action, Aug. 2, 2010, Guangwen Wei, U.S. Appl. No. 12/369,005, filed Feb. 11, 2009.
Bingfa et al., 2009, "Anti-Hepatitis B Virus Activity and Mechanisms of Recombinant Human Serum Albumin-Interferon-α-2b Fusion Protein in vitro and in vivo", Pharmacology, 83:323-332.
Wong, Samson S.Y. and Yuen, Kwok-Yung, 2008, "The management of coronavirus infections with particular reference to SARS", Journal of Antimicrobial Chemotherapy, 62:437-441.
Zheng, B. et al., 2004, "Potent inhibition of SARS-associated coronavirus (SCOV) infection and replication by type I interferons (IFN-alpha/beta) but not by type II interferon (IFN-gamma)," J. Interferon Cytokine Res., 24(7):288-90. [Abstract only].
European Examiner's Report, Jan. 14, 2011, Sichuan Biotechnology Research Center, European Patent Application No. EP 04809634.1, Filed Mar. 23, 2006.
Japanese Examiner's Report, Dec. 28, 2010, Sichuan Biotechnology Research Center, Japanese Patent Application No. 2006-524916, Filed Feb. 27, 2006.
U.S. Office Action, Dec. 17, 2010, for Guangwen Wei, U.S. Appl. No. 12/246,153, filed Oct. 6, 2008.

U.S. Office Action, Dec. 22, 2010, for Guangwen Wei, U.S. Appl. No. 12/554,297, filed Sep. 4, 2009.
Canadian Office Action, Mar. 8, 2011, Sichuan Biotechnolgy Research Center, Canadian Application No. 2,439,503, Filed Aug. 27, 2003.
Krogsgaard et al., 1996, "Relation between efficacy and cumulative dose of alpha interferon in chronic hepatitis B. European Concerted Action on Viral Hepatitis (Eurohep)", J Hepatology, 25(6):795-802.
Jia, Liu Yun-peng, et al., 2007, "Meta-analysis of induction chemotherapy combined with interferon in small lung cancer", Chinese Journal of Practical Internal Medicine, 613-616.
Jin Bo et al., 2006, "Meta-analysis of induction chemotherapy combined with interferon in Advanced Non-small Cell Lung Cancer", Department of Medical Oncology, the First Affiliated Hospital of China Medical University, Shenyang 110001, China. pp. 370-375.
Hu Xue-jun et al., 2006, "Meta-analysis of Maintenance Therapy With Interferon for Small Cell Lung Cancer", Chin J Evid-based Med, 6(11):809-814.
Australian Office Action, Mar. 28, 2011, Guangwen Wei, Australian Application No. 2006257286, Filed Aug. 8, 2007.
U.S. Office Action, Dec. 29, 2009, Wei et al., U.S. Appl. No. 12/105,455, filed Apr. 18, 2008.
U.S. Notice of Allowance, Jul. 29, 2010, for Guangwen Wei, U.S. Appl. No. 12/105,455, filed Apr. 18, 2008.
Australian Office Action, Oct. 3, 2011,Guangwen Wei, Australia Application No. 2006257286, Filed Aug. 8, 2007.
U.S. Office Action,Oct. 11, 2011,Guangwen Wei, U.S. Appl. No. 12/105,455, filed Apr. 18, 2008.
EPO Office Action, Oct. 25, 2011,Huiyangtech (USA), Inc., Application No. EP 04809634,Filed Aug. 26,2004.
Indian Office Action, Oct. 25, 2011,Guangwen Wei, Indian Application No. 1214/MUMNP/2007,Filed Aug. 13, 2007.
Chinese Decision About the Reexamination,Nov. 10, 2011,Guangwen Wei,Chinese Application No. 200680007733.1,Filed Mar. 9, 2006.
Korean Office Action, Oct. 28, 2011,Guangwen Wei, Korean Application No. 10-2006-7003699,Filed Feb. 23, 2006.
Japanese Decision of Rejection,Feb. 1, 2012,Guangwen Wei, Japanese Application No. 2006-524916 Filed Apr. 18, 2008.
CAS No. 118390-30-0 (Jan. 13, 1989, STN entry date).
Supplementary European Search report,Feb. 23, 2012,Guangwen Wei,European Application No. 06795349.7 Filed Oct. 4, 2007.
Overexpression of a synthetic gene encoding human alpha interferon in *Escherichia coli*,Protein Expression & purification 35(2004) 353-359.
Improvement of human interferon HUIFNα2 and HCV core protein expression levels in *Escherichia coli* but not of HUIFNα8 by using the tRNA AGA/AGG,BBRC,296(2002) 1303-1309.
Expression of synthetic human interferon-α1 gene with modified nucleotide sequence in mammalian cells,Gene,46(1986) 89-95.
WO 02/10411 A2,Feb. 7,2002,Application No. PCT/EP01/08660,Filed Jul. 21, 2001.
Chinese Office Action, Notification of Grant,Mar. 2, 2012,Chinese Application No. 200680007733.1,Filed Mar. 9, 2006.
Taiwan Official Letter,Apr. 27, 2012,Guangwen Wei,Taiwan Application No. 95107930,Filed Mar. 9,2006.
Malaysia Office Action,Apr. 30, 2012,Guangwen Wei,MY Application No. 20061015, Filed Mar. 9, 2006.
U.S.A. Office Action,Notice of Allowance and Fees,Jun. 13 ,2012,Guangwen Wei, U.S. Appl. No. 12/554,297, filed Sep. 4, 2009.
U.S.A. Office Action,Restriction Requirement,Jul. 13, 2012,Guangwen Wei, U.S. Appl. No. 12/905,149, filed Oct. 15, 2010.
Korean Final Refusal,Jul. 13, 2012,Guangwen Wei, Korean Application No. 10-2006-7003699,Filed Feb. 23, 2006.
Australian Office Action,Notice of acceptance,Jul. 25, 2012,Guangwen Wei,Australian Application No. 2011202683, Filed Jun. 6, 2011.
Australian Office Action,Notice of acceptance,Aug. 1, 2012,Guangwen Wei,Australian Application No. 2006257286, Filed Mar. 9, 2006.
Canadian Examiner's Report,Aug. 9, 2012,Guangwen Wei,Canadian Application No. 2597317,Filed Aug. 9, 2007.
U.S.A. Office Action,Aug. 13, 2012,Guangwen Wei, U.S. Appl. No. 11/817,926, filed Sep. 6,2007.
Boshoff et al, 2002. CA Nature Reviews Cancer. 2 373-382.
Japanese Decision of Rejection,Sep. 5, 2012,Guangwen Wei, Japanese Application No. 2008-500294,Filed Sep. 6, 2007.
Ho et al., "Recombinant human interferon alfa-A supresses HTLV-III replication in vitro", The Lancet, (Mar. 16, 1985), vol. 325, No. 8429, p. 602-604.
Masao Ito, et al., "Human T cell leukemia virus", Medical Dictionary of Igaku-Shyoin, Igaku-Shyoin (Mar. 1, 2003), version 1, p. 2061.
U.S.A. Office Action,lssue Notification,Sep. 26, 2012, U.S. Appl. No. 12/554,297, filed Sep. 4, 2009.

Figure 1

```
5'           11         21         31         41         51
+1  M  C  D  L  P  Q  T  H  S  L  G  N  R  R  A  L  I  L  L  A
  1 ATGTGCGACC TGCCGCAGAC CCACTCCCTG GGTAACCGTC GTGCTCTGAT CCTGCTGGCT
    TACACGCTGG ACGGCGTCTG GGTGAGGGAC CCATTGGCAG CACGAGACTA GGACGACCGA

5'           71         81         91        101        111
+1  Q  M  R  I  S  P  F  S  C  L  K  D  R  H  D  F  G  F  P
 61 CAGATGCGTC GTATCTCCCC GTTCTCCTGC CTGAAAGACC GTCACGACTT CGGTTTCCCG
    GTCTACGCAG CATAGAGGGG CAAGAGGACG GACTTTCTGG CAGTGCTGAA GCCAAAGGGC

5'          131        141        151        161        171
+1   Q  E  E  F  D  G  N  Q  F  Q  K  A  Q  A  I  S  V  L  H  E
121 CAGGAAGAAT TCGACGGTAA CCAGTTCCAG AAAGCTCAGG CTATCTCCGT TCTGCACGAA
    GTCCTTCTTA AGCTGCCATT GGTCAAGGTC TTTCGAGTCC GATAGAGGCA AGACGTGCTT

5'          191        201        211        221        231
+1   M  I  Q  Q  T  F  N  L  F  S  T  K  D  S  S  A  A  W  D  E
181 ATGATCCAGC AGACCTTCAA CCTGTTCTCC ACCAAAGACT CCTCCGCTGC TTGGGACGAA
    TACTAGGTCG TCTGGAAGTT GGACAAGAGG TGGTTTCTGA GGAGGCGACG AACCCTGCTT

5'          251        261        271        281        291
+1   S  L  L  E  K  F  Y  T  E  L  Y  Q  Q  L  N  D  L  E  A  C
241 TCCCTGCTGG AAAAATTCTA CACCGAACTG TACCAGCAGC TGAACGACCT GGAAGCTTGC
    AGGGACGACC TTTTTAAGAT GTGGCTTGAC ATGGTCGTCG ACTTGCTGGA CCTTCGAACG

5'          311        321        331        341        351
+1   V  I  Q  E  V  G  V  E  E  T  P  L  M  N  V  D  S  I  L  A
301 GTTATCCAGG AAGTTGGTGT TGAAGAAACC CCGCTGATGA ACGTTGACTC CATCCTGGCT
    CAATAGGTCC TTCAACCACA ACTTCTTTGG GGCGACTACT TGCAACTGAG GTAGGACCGA

5'          371        381        391        401        411
+1   V  K  K  Y  F  Q  R  I  T  L  Y  L  T  E  K  K  Y  S  P  C
361 GTTAAAAAAT ACTTCCAGCG TATCACCCTG TACCTGACCG AAAAAAAATA CTCCCCGTGC
    CAATTTTTTA TGAAGGTCGC ATAGTGGGAC ATGGACTGGC TTTTTTTTAT GAGGGGCACG

5'          431        441        451        461        471
+1   A  W  E  V  V  R  A  E  I  M  R  S  F  S  L  S  T  N  L  Q
421 GCTTGGGAAG TTGTTCGTGC TGAAATCATG CGTTCCTTCT CCCTGTCCAC CAACCTGCAG
    CGAACCCTTC AACAAGCACG ACTTTAGTAC GCAAGGAAGA GGGACAGGTG GTTGGACGTC

5'          491        501
+1   E  R  L  R  R  K  #    (SEQ ID NO:2)
481 GAACGTCTGC GTCGTAAAGA ATAA    (SEQ ID NO:1)
    CTTGCAGACG CAGCATTTCT TATT    (SEQ ID NO:15)
```

Figure 2

```
     5'         11          21          31          41          51
+1  M   C   D   L   P   Q   T   H   S   L   G   N   R   R   A   L   I   L   L   A
  1 ATGTGTGATT TACCTCAAAC TCATTCTCTT GGTAACCGTC GCGCTCTGAT TCTGCTGGCA
    TACACACTAA ATGGAGTTTG AGTAAGAGAA CCATTGGCAG CGCGAGACTA AGACGACCGT

5'         71          81          91         101         111
+1  Q   M   R   R   I   S   P   F   S   C   L   K   D   R   H   D   F   G   F   P
 61 CAGATGCGTC GTATTTCCCC GTTTAGCTGC CTGAAAGACC GTCACGACTT CGGCTTTCCG
    GTCTACGCAG CATAAAGGGG CAAATCGACG GACTTTCTGG CAGTGCTGAA GCCGAAAGGC

5'        131         141         151         161         171
+1   Q   E   E   F   D   G   N   Q   F   Q   K   A   Q   A   I   S   V   L   H   E
121 CAAGAAGAGT TCGATGGCAA CCAATTCCAG AAAGCTCAGG CAATCTCTGT ACTGCACGAA
    GTTCTTCTCA AGCTACCGTT GGTTAAGGTC TTTCGAGTCC GTTAGAGACA TGACGTGCTT

5'        191         201         211         221         231
+1  M   I   Q   Q   T   F   N   L   F   S   T   K   D   S   S   A   A   W   D   E
181 ATGATCCAAC AGACCTTCAA CCTGTTTTCC ACTAAAGACA GCTCTGCTGC TTGGGACGAA
    TACTAGGTTG TCTGGAAGTT GGACAAAAGG TGATTTCTGT CGAGACGACG AACCCTGCTT

5'        251         261         271         281         291
+1   S   L   L   E   K   F   Y   T   E   L   Y   Q   Q   L   N   D   L   E   A   C
241 AGCTTGCTGG AGAAGTTCTA CACTGAACTG TATCAGCAGC TGAACGACCT GGAAGCATGC
    TCGAACGACC TCTTCAAGAT GTGACTTGAC ATAGTCGTCG ACTTGCTGGA CCTTCGTACG

5'        311         321         331         341         351
+1   V   I   Q   E   V   G   V   E   E   T   P   L   M   N   V   D   S   I   L   A   (SEQ ID NO:4)
301 GTAATCCAGG AAGTTGGTGT AGAAGAGACT CCGCTGATGA ACGTCGACTC TATTCTGGCA
                                                                      (SEQ ID NO:3)
    CATTAGGTCC TTCAACCACA TCTTCTCTGA GGCGACTACT TGCAGCTGAG ATAAGACCGT
                                                                      (SEQ ID NO:16)
```

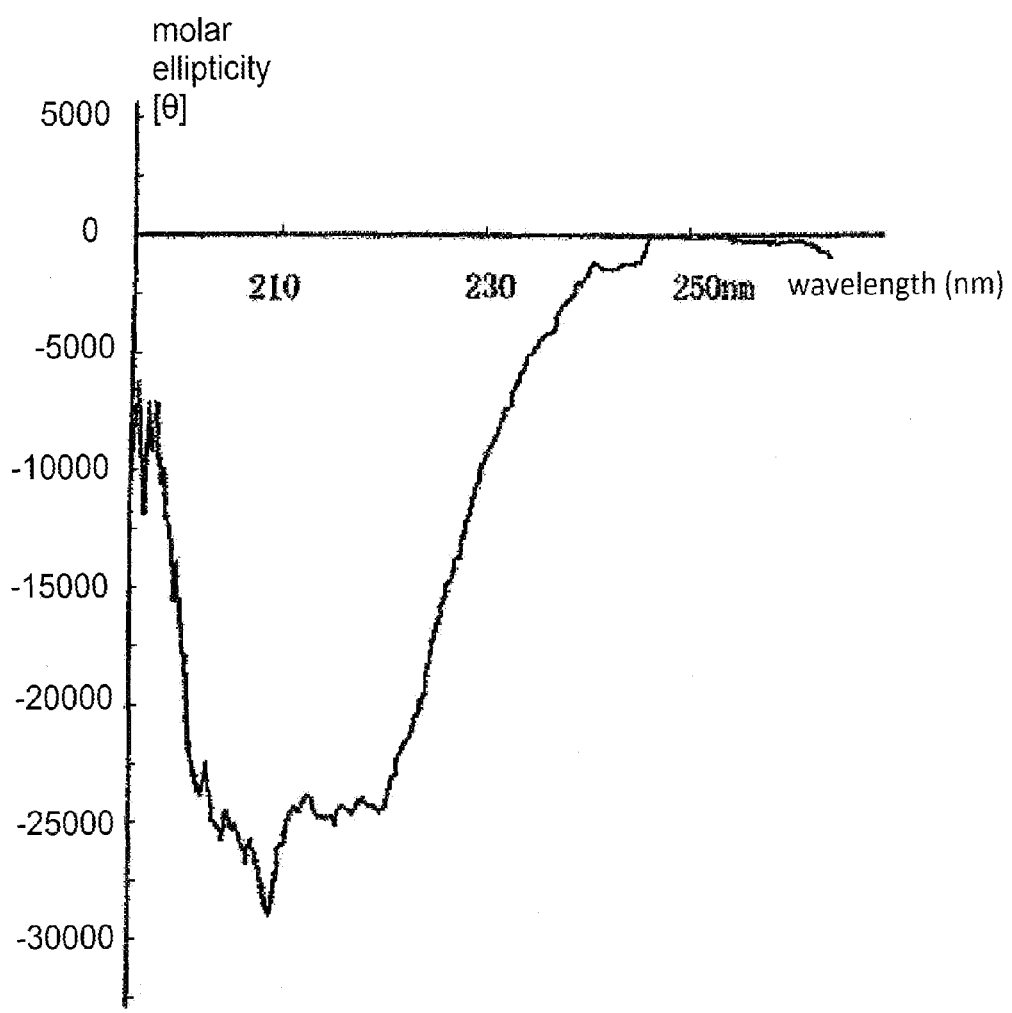
Figure 6-A

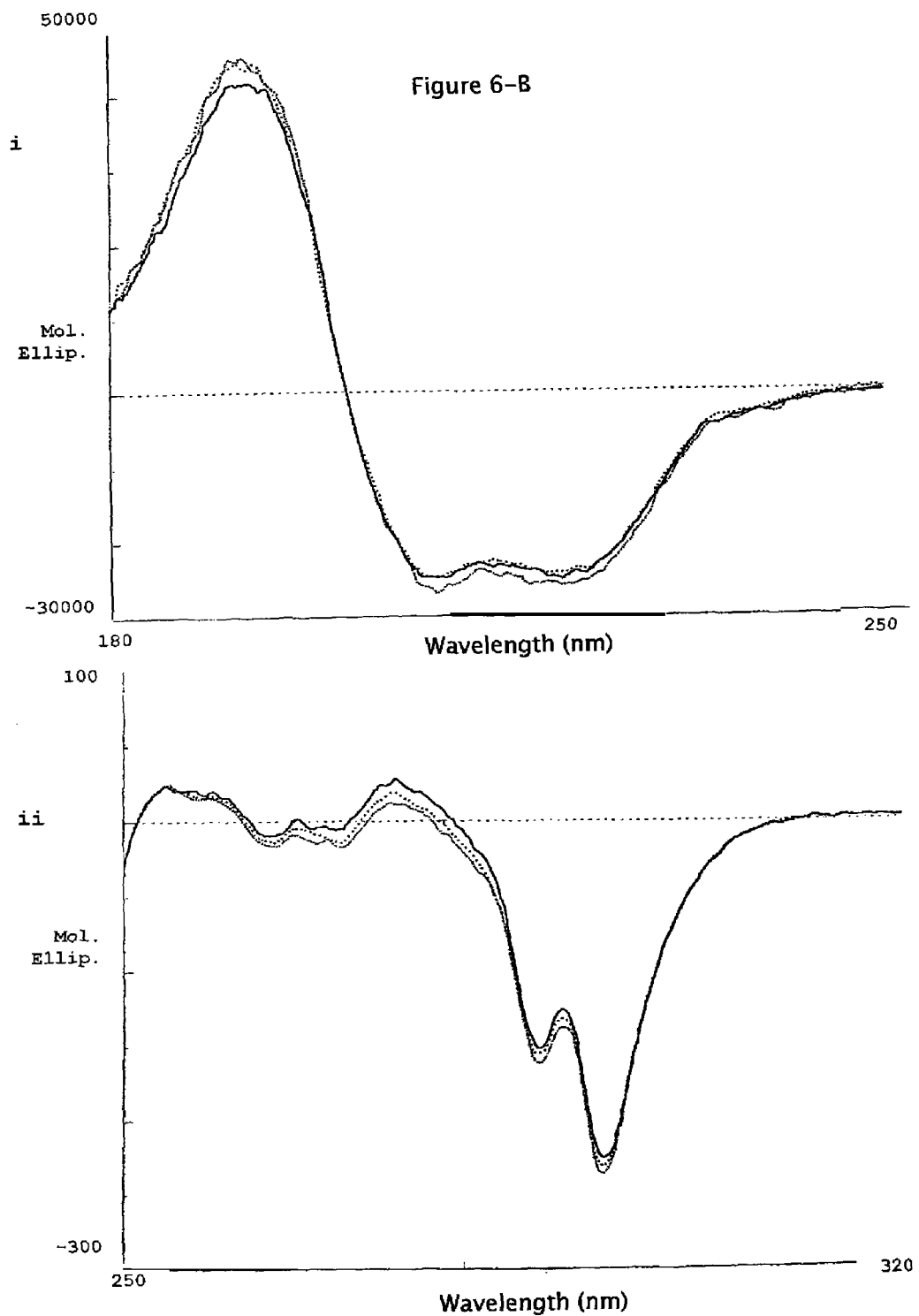

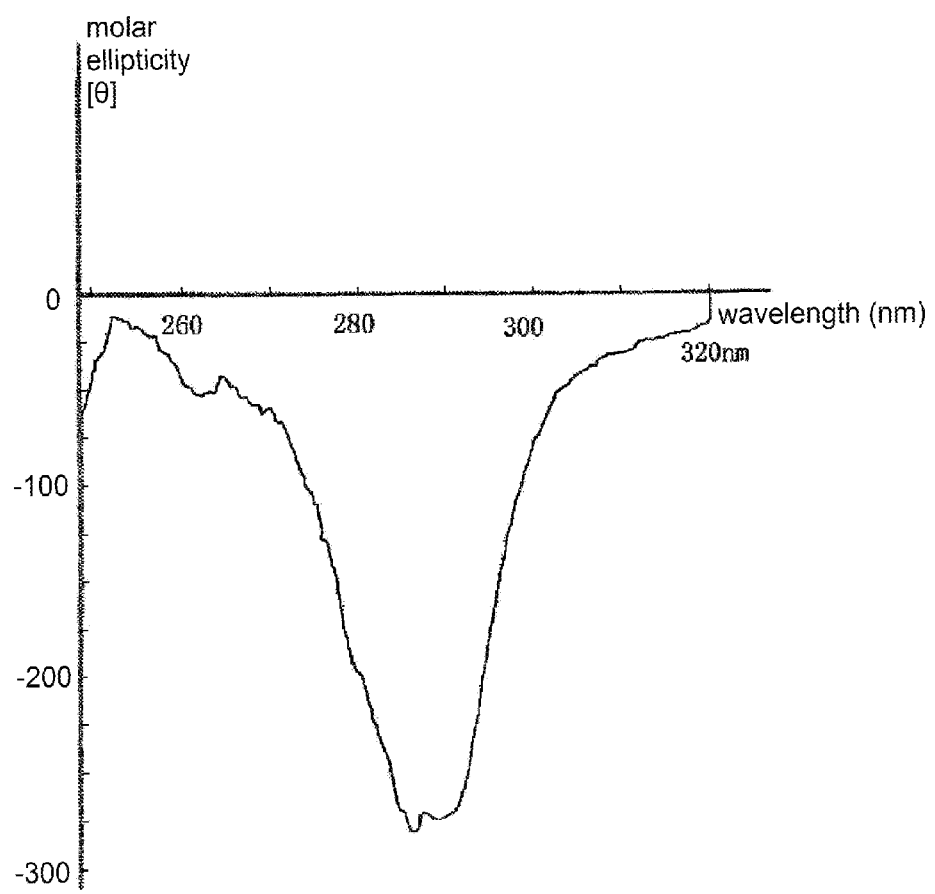
Figure 6-C

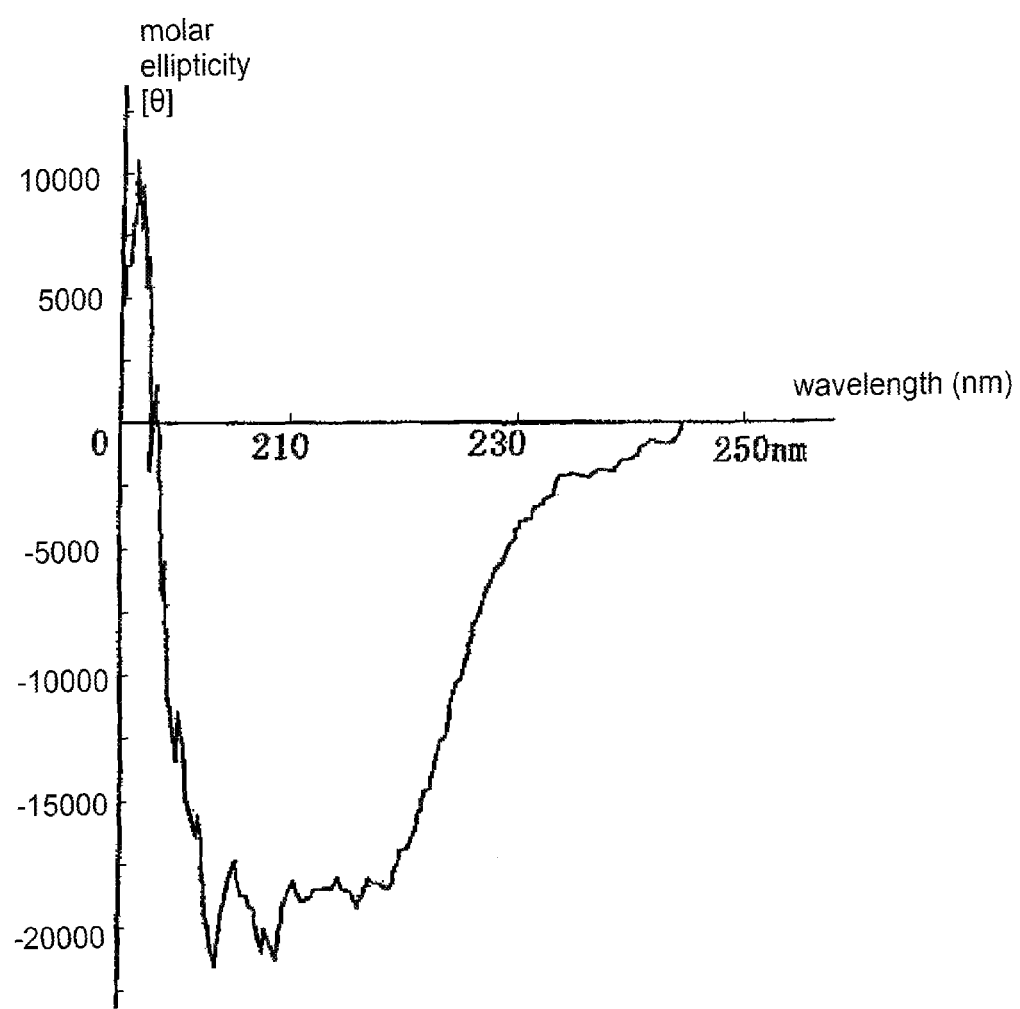
Figure 6-D

TREATMENT OF TUMORS WITH RECOMBINANT INTERFERON ALPHA

This application is a continuation of U.S. Ser. No. 12/105,455, filed Apr. 18, 2008 which is a continuation of U.S. Ser. No. 10/650,365, filed Aug. 28, 2003 which claims priority of International Patent Application No. PCT/CN02/00128, filed on Feb. 28, 2002, which claims priority of Chinese Application No. 01104367.9, filed on Feb. 28, 2001, the contents of which are incorporated by reference here into this application.

Throughout this application, various references are referred to. Disclosures of these publications in their entireties are hereby incorporated by reference into this application in order to more fully describe the state of the art to which this invention pertains.

FIELD OF THE INVENTION

This invention is related to a recombinant super-compound interferon (rSIFN-co) with changed spatial configuration. One characteristic of rSIFN-co in this invention is that it cannot only inhibit DNA (deoxyribonucleic acid) duplication of the hepatitis B virus but also the secretion of HBsAg and HBeAg.

BACKGROUND OF THE INVENTION rSIFN-co is a new interferon molecule constructed with the most popular conservative amino acid found in natural human α-IFN subtypes using genetic engineering methods. U.S. Pat. Nos. 4,695,623 and 4,897,471 have described it. rSIFN-co had been proved to have broad-spectrum IFN activity and virus- and tumor-inhibition and natural killer cell activity. U.S. Pat. No. 5,372,808 by Amgen, Inc. addresses treatment rSIFN-co. Chinese Patent No. 97193506.8 by Amgen, Inc. addresses re-treatment of rSIFN-co on hepatitis C. Chinese Patent No. 98114663.5 by Shenzhen Jiusheng Bio-engineering Ltd. addresses treatment of rSIFN-co on hepatitis B and hepatitis C.

The United States Food and Drug Administration (FDA) authorized Amgen to produce rSIFN-co with *E. Coli.* for clinical hepatitis C treatment at the end of 1997.

Hepatitis B patients can be identified when detecting HBsAg and the HBeAg. α-IFN is commonly used in clinics to treat hepatitis B. IFN binds superficial cell membrane receptors, inhibiting DNA and RNA (ribonucleic acid) duplication, including inducing some enzymes to prevent duplication of the virus in hepatitis-infected cells. All IFNs can inhibit only the DNA duplication of viruses, not the e and s antigen.

This disclosure describes recombinant super-compound interferon, method to produce the same and uses thereof.

SUMMARY OF THE INVENTION

This invention provides a recombinant super-compound interferon or an equivalent thereof with changed spatial configuration. An equivalent is a molecule which is similar in function to the super-compound interferon. The super-compound interferon possesses anti-viral or anti-tumor activity. This invention also provides an artificial gene codes for the super-compound interferon or its equivalent.

This invention provides a process for production of recombinant super-compound interferon comprising introducing an artificial gene with selected codon preference into an appropriate host, culturing said introduced host in an appropriate condition permitting expression of said super-compound interferon and harvesting the expressed super-compound interferon.

This invention provides a composition comprising the recombinant super-compound interferon or its equivalent and a suitable carrier. This invention further provides a pharmaceutical composition comprising the recombinant super-compound interferon or its equivalent and a pharmaceutically acceptable carrier.

This invention provides a method for treating viral diseases or tumor in a subject comprising administering to the subject an effective amount of the super-compound interferon or its equivalent.

This invention provides the above-described method wherein super-compound interferon was administered via oral, vein injection, muscle injection, peritoneal injection, subcutaneous injection, nasal, mucosal administration, by inhalation via an inspirator.

DETAILED DESCRIPTION OF THE FIGURES

Figure 4:
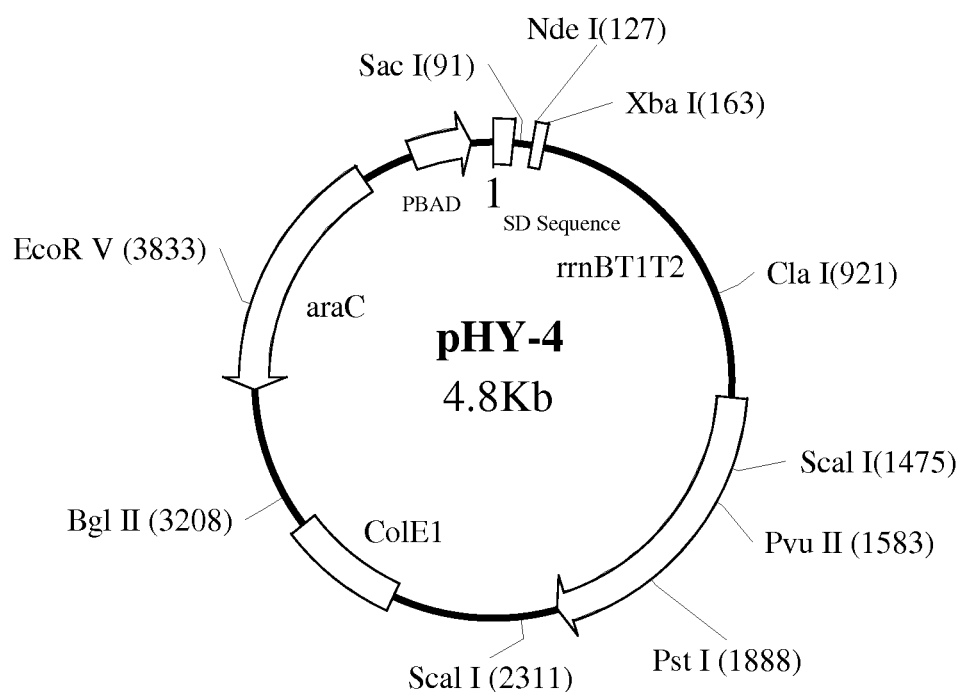
Figure 5:
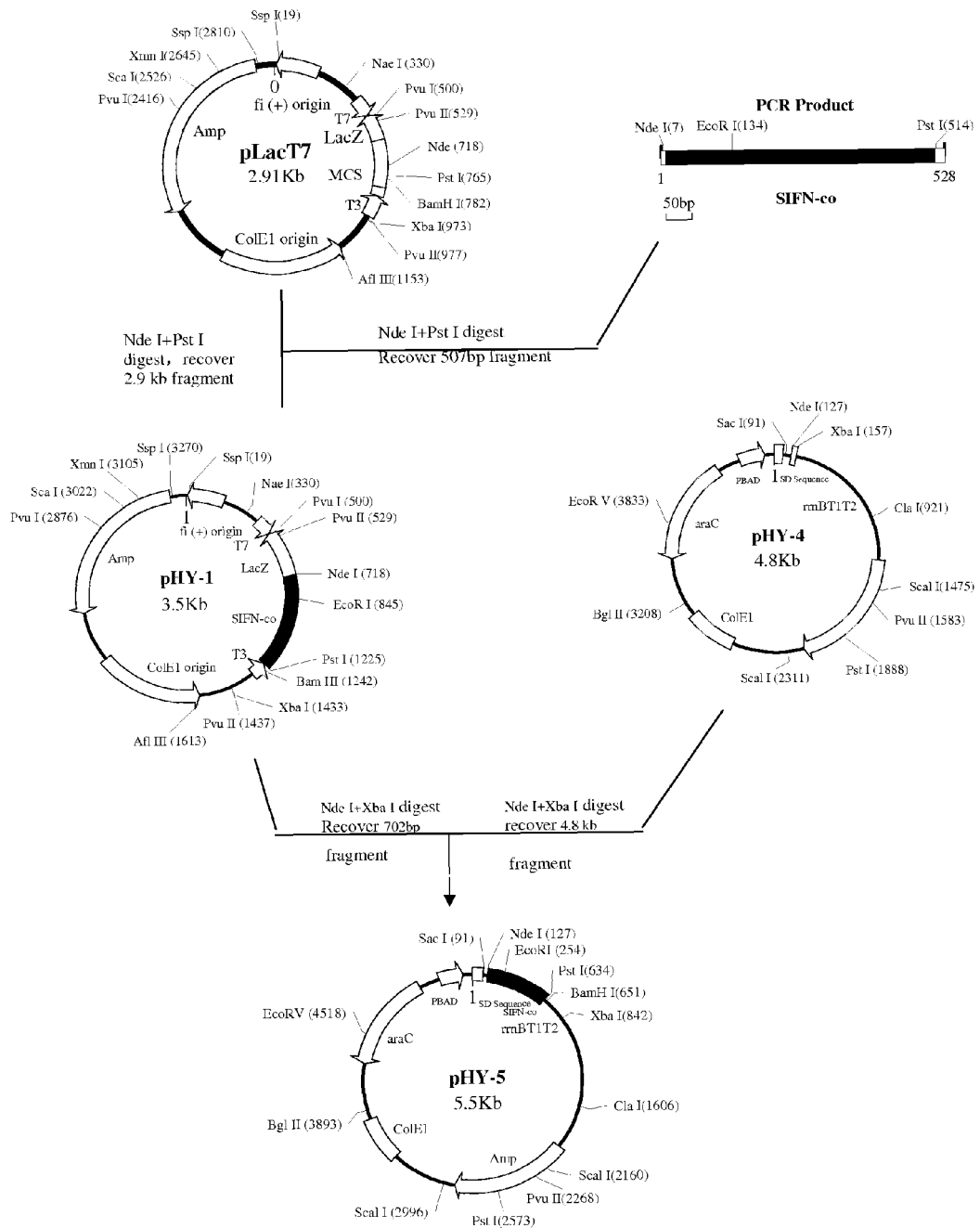

FIG. 1. rSIFN-co cDNA sequence designed according to *E. Coli.* codon usage and deduced rSIFN-co amino acid sequence FIG. 2. Sequence of another super-compound interferon FIG. 3. Diagram of pLac T7 cloning vector plasmid FIG. 4. Diagram of pHY-4 expression vector plasmid FIG. 5. Construction process of expression plasmid pHY-5

FIG. 6-A. Circular Dichroism spectrum of Infergen®
Spectrum range: 250 nm-190 nm
Sensitivity: 2 m°/cm
Light path: 0.20 cm
Equipment: Circular Dichroism J-500C
Samples: contains 30 µg/ml IFN-con1, 5.9 mg/ml of NaCl and 3.8 mg/ml of $Na_2PO_4$, pH7.0.

Infergen® (interferon alfacon-1), made by Amgen Inc., also known as consensus interferon, is marketed for the treatment of adults with chronic hepatitis C virus (HCV) infections. It is currently the only FDA approved, bio-optimized interferon developed through rational drug design and the only interferon with data in the label specifically for non-responding or refractory patients. InterMune's sales force re-launched Infergen® in January 2002 with an active campaign to educate U.S. hepatologists about the safe and appropriate use of Infergen®, which represents new hope for the more than 50 percent of HCV patients who fail other currently available therapies.

FIG. 6-B. Circular Dichroism spectrum of Infergen® From Reference [Journal of Interferon and Cytokine Research. 16:489-499 (1996)]

FIG. 6-C. Circular Dichroism spectrum of rSIFN-co
Spectrum range: 320 nm-250 nm
Sensitivity: 2 m°/cm
Light path: 2 cm
Equipment: Circular Dichroism J-500C
Samples: contains 0.5 mg/ml rSIFN-co, 5.9 mg/ml of NaCl and 3.8 mg/ml of $Na_2PO_4$, pH7.0.

FIG. 6-D. Circular Dichroism spectrum of rSIFN-co
Spectrum range: 250 nm-190 nm
Sensitivity: 2 m°/cm
Light path: 0.20 cm
Equipment: Circular Dichroism J-500C
Samples: contains 30 µg/ml rSIFN-co, 5.9 mg/ml of NaCl and 3.8 mg/ml of $Na_2PO_4$, pH7.0.

Clearly, as evidenced by the above spectra, the secondary or even tertiary structure of rSIFN-co is different from Infergen®.

DETAILED DESCRIPTION OF THE INVENTION

This invention provides a recombinant super-compound interferon or an equivalent thereof with changed spatial configuration. This invention reveals that protein with same primary sequence might have different biological activities. As illustrated in the following example, this invention disclosed two proteins with identical amino acid sequence but with different activities. This activity may sometimes become improved efficacy and sometimes, the protein with changed spatial configuration would reveal new function.

An equivalent is a molecule which is similar in function to the compound interferon. An equivalent could be a deletion, substitution, or replacement mutant of the original sequence. Alternatively, it is also the intention of this invention to cover mimics of the recombinant super-compound interferon. Mimics could be a peptide, polypeptide or a small chemical entity.

The interferon described herein includes but is not limited to interferon α, β, or ω. In an embodiment, it is IFN-1a, IFN-2b or other mutants.

In an embodiment, the super-compound interferon disclosed has higher efficacy than the interferon described in U.S. Pat. Nos. 4,695,623 or 4,897,471. This super-compound interferon is believed to have unique secondary or tertiary structure. (See e.g. FIG. 6)

The super-compound interferon described herein has spatial structure change(s) resulting from the changes of its production process.

The above-described super-compound interferon may be produced by a high efficiency expression system which uses a special promoter. In an embodiment, the promoter is $P_{BAD}$. As it could be easily appreciated by other ordinary skilled artisan, other inducible promoter, such as heat shock promoter, may be used in this invention.

The super-compound interferon may also be produced with its gene as artificially synthesized cDNA with adjustment of its sequence from the wild-type according to codon preference of E. Coli. Extensive discussion of said codon usage (preference) may be found in U.S. Pat. No. 4,695,623. See e.g. column 6, line 41—column 7, line 35

The above described super-compound interferon possesses anti-viral or anti-tumor activity and therefore useful in preventing and treating viral diseases, tumors or cancers.

The virus diseases include but are not limited to hepatitis A, hepatitis B, hepatitis C, other types of hepatitis, infections caused by Epstein-Barr virus, Cytomegalovirus, herpes simplex viruses, other herpes viruses, papovaviruses, poxviruses, picornaviruses, adenoviruses, rihnoviruses, human T cell leukaemia viruses I, human T cell leukaemia viruses II, or human T cell leukemia viruses III.

Therefore, this invention provides a method for inhibiting virus replication or virus infected cells by contacting said virus or infected cells with an effective amount of the super-compound interferon or its equivalent. This super-compound interferon is useful in preventing or treating the following cancers or tumors:

| Cancer | Skin Cancer | Basal Cell Carcinoma |
| --- | --- | --- |
| | | Malignant Melanoma |
| | Renal cell carcinoma | |
| | Liver Cancer | |
| | Thyroid Cancer | |
| | Rhinopharyngeal Cancer | |
| | Solid Carcinoma | Prostate Cancer |
| | | Tummy Cancer |
| | | Esophagus Cancer |
| | | Rectal Cancer |
| | | Pancreas Cancer |
| | | Mammary Cancer |
| | Ovarian Cancer & Superficial Bladder Cancer | |
| | Hemangioma | |
| | Epidermoid Carcinoma | Cervical Cancer |
| | | Non-small Cell Lung Cancer |
| | | Small Cell Lung Cancer |
| | | Glioma |
| Malignant Hemal Disease | Leucocythemia | Acute Leucocythemia |
| | | Chronic Leucocythemia |
| | Chronic Myelocytic Leukemia | |
| | Hairy Cell Leukemia | |
| | Lymphadenoma | |
| | Multiple Myeloma | |
| | Polycythemia Vera | |
| Others | Kaposi's Sarcoma | |

Accordingly, this invention provides a method for inhibiting tumor or cancer cell growth by contacting the super-compound interferon or its equivalent with said tumor or cancer cells. In a further embodiment, the super-compound interferon inhibits the DNA duplication and secretion of HBsAg and HBeAg of Hepatitis B Virus.

This invention also provides an artificial gene codes for the super-compound interferon or its equivalent. It is within the ordinary skill to design an artificial gene. Many methods for generating nucleotide sequence and other molecular biology techniques have been described previously. See for example, Joseph Sambrook and David W. Russell, Molecular Cloning: A laboratory Manual, December 2000, published by Cold Spring Harbor Laboratory Press.

This invention provides a vector comprising the gene which codes for the super-compound interferon or its equivalent.

This invention provides an expression system comprising the vector comprising the gene which codes for the super-compound interferon or its equivalent. The cells include but are not limited to prokaryotic or eukaryotic cells.

This invention also provides a host cell comprising the vector comprising the gene which codes for the super-compound interferon or its equivalent.

This invention provides a process for production of recombinant super-compound interferon comprising introducing an artificial gene with selected codon preference into an appropriate host, culturing said introduced host in an appropriate condition for the expression of said compound interferon and harvesting the expressed compound interferon.

The process may comprise extraction of super-compound interferon from fermentation broth, collection of inclusion body, denaturation and renaturation of the harvested protein.

The process may maintain the high efficacy even when the super-compound interferon is used with an agent and in a particular concentration. The process also comprises separation and purification of the super-compound interferon. The process further comprises lyophilization of the purified super-compound interferon. The process comprises production of liquid injection of super-compound interferon.

This invention also provides the produced super-compound interferon by the above processes.

This invention provides a composition comprising the recombinant super-compound interferon or its equivalent and a suitable carrier.

This invention provides a pharmaceutical composition comprising the recombinant super-compound interferon or its equivalent and a pharmaceutically acceptable carrier.

This invention provides a method for treating viral diseases or tumor in a subject comprising administering to the subject an effective amount of the super-compound interferon or its equivalent.

This invention provides the above-described method wherein the viral diseases is hepatitis A, hepatitis B, hepatitis C, other types of hepatitis, infections of viruses caused by Epstein-Barr virus, Cytomegalovirus, herpes simplex viruses, or other type of herpes viruses, papovaviruses, poxviruses, picornaviruses, adenoviruses, rihnoviruses, human T cell leukaemia viruses I, or human T cell leukaemia viruses II, or human T cell leukemia virus III.

This invention provides the above-described method wherein super-compound interferon was administered via oral, vein injection, muscle injection, peritoneal injection, subcutaneous injection, nasal, mucosal administration, by inhalation via an inspirator.

This invention provides the above-described method wherein super-compound interferon was administered following the protocol of injection 9 μg or 15 μg per day, 3 times a week, total 24 weeks.

It was surprising to find that rSIFN-co, the spatial structure of which has been changed, is not only a preparation to inhibit the DNA duplication of hepatitis B, but to inhibit the secretion of HBsAg and HBeAg on 2.2.15 cells.

One objective of this invention is to offer a preparation of rSIFN-co to directly inhibit the DNA duplication of hepatitis B viruses and the secretion of HBeAg and HBsAg of hepatitis B and decrease them to normal levels.

In one of the results of this invention, rSIFN-co was produced with recombinant techniques. On the condition of fixed amino acid sequence, the IFN DNA was redesigned according to the *E. Coli.* codon usage and then the rSIFN-co gene was artificially synthesized. rSIFN-co cDNA was cloned into the high-expression vector of *E. Coli.* by DNA recombinant techniques, and a high expression of rSIFN-co was gained by using of induce/activate-mechanism of L-arabinose to activate the transcription of $P_{BAD}$ promoter.

Compared with usual thermo-induction, pH induction and IPTG induction systems of genetic engineering, arabinose induction/activation system has some advantages: (1) Common systems relieve promoter function by creating a "derepression" pattern. Promoters then induce downstream gene expression. So temperature and pH change and the addition of IPTG cannot activate promoters directly. In the system disclosed herein, L-arabinose not only deactivates and represses but also activates the transcription of $P_{BAD}$ promoter which induce a high expression of rSIFN-co. Therefore, the arabinose induction/activation system is a more effective expression system. (2) The relation between Exogenous and L-arabinose dosage is linearity. This means the concentration of arabinose can be changed to adjust the expression level of the exogenous gene. Therefore, it is easier to control the exogenous gene expression level in *E. Coli.* by arabinose than by changing temperature and pH value. This characteristic is significant for the formation of inclusion bodies. (3) L-arabinose is resourceful cheap and safe, which, on the contrary, are the disadvantages of other inducers such as IPTG.

This embodiment creates an effective and resistant rSIFN-co-expressing *E. Coli.* engineering strain with an L-arabinose induction/activation system. The strain is cultivated and fermented under suitable conditions to harvest the bacterial bodies. Inclusion bodies are then purified after destroying bacteria and washing repeatedly. The end result, mass of high-purity, spatial-configuration-changed rSIFN-co protein for this invention and for clinical treatment, was gained from denaturation and renaturation of inclusion bodies and a series of purification steps.

The following are some rSIFN-co preparations: tablets, capsules, oral liquids, pastes, injections, sprays, suppositories, and solutions. Injections are recommended. It is common to subcutaneously inject or vein-inject the medicine. The medicine carrier could be any acceptance medicine carrier, including carbohydrate, cellulosum, adhesive, collapse, emollient, filling, add-dissolve agent, amortization, preservative, add-thick agent, matching, etc.

This invention also provides a pharmaceutical composition comprising the above composition and a pharmaceutically acceptable carrier.

For the purposes of this invention, "pharmaceutically acceptable carriers" means any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, etc. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

This invention will be better understood from the examples which follow. However, one skilled in the art will readily appreciate that the specific methods and results discussed are merely illustrative of the invention as described more fully in the claims which follow thereafter.

EXPERIMENTAL DETAILS

Example 1 rSIFN-co is a new interferon molecule constructed according to conservative amino acid in human IFN-α subtype with genetic engineering method. It has been proven that rSIFN-co has broad-spectrum IFN activity, such as high antivirus and tumor inhibition activity, especially for effectively treating hepatitis C.

*E. Coli.* codon was used to redesign rSIFN-co cDNA and then artificially synthesize cDNA of rSIFN-co from published rSIFN-co DNA sequences and deduced amino acid sequences (FIG. 1).

In order to get pure rSIFN-co protein, rSIFN-co cDNA was cloned into *E. Coli.* high-expression vector, and L-arabinose, which can activate strong $P_{BAD}$ promoter in vectors, was used to induce high expression of rSIFN-co gene.

Synthesis of *E. Coli.* cDNA Sequence

Redesign of rSIFN-co cDNA Sequence rSIFN-co cDNA was redesigned according to the codon usage of *E. Coli.* to achieve high expression in *E. Coli.* Deduced amino acid sequence from the redesigned cDNA sequence of rSIFN-co is completely coincidental with primitive amino acid sequence of published rSIFN-co (FIG. 1).

rSIFN-co cDNA Sequence Synthesis rSIFN-co cDNA 5'-Terminus and 3'-Terminus Semi-Molecular Synthesis Two semi-moleculars can be directly synthesized: rSIFN-co cDNA 5'-terminus 280 bp (fragment I) and 3'-terminus 268 bp (fragment II) by PCR. There are 41 bp overlapping among fragment II and fragment I.

(1) Chemical Synthesis Oligodeoxynucleotide Fragment:

Oligomer A (SEQ ID NO:5):

5'ATGTGCGACCTGCCGCAGACCCACTC-CCTGGGTAACCGTCGTGCTCTGATCCT-GCTGGCTCA GATGCGTCGTATCTCCCCGTTCTC-CTGCCTGAAAGACCGTCACGAC3'

Oligomer B (SEQ ID NO:7):

5'CTGAAAGACCGTCACGACTTCGGTTTC-CCGCAGGAAGAATTCGACGGTAACCAGTTCCAG AAAGCTCAGGCTATCTCCGTTCTGCAC-GAAATGATCCAGCAGACCTTC3'

Oligomer C (SEQ ID NO:8):

5'GCTGCTGGTACAGTTCGGTGTA-GAATTTTTCCAGCAGGGATTCGTC-CCAAGCAGCGGAGGAG TCTTTGGTGGAGAA-CAGGTTGAAGGTCTGCTGGATCATTTC3'

Oligomer D (SEQ ID NO:9):

5'ATCCCTGCTGGAAAAATTCTACAC-CGAACTGTACCAGCAGCTGAACGACCTG-GAAGCTTGCG TTATCCAGGAAGTTGGTGTTGAA-GAAACCCCGCTGATGAAC3'

Oligomer E (SEQ ID NO:10):

5'GAAGAAACCCCGCTGATGAACGT-TGACTCCATCCTGGCTGT-TAAAAAATACTTCCAGCGTAT CACCCTGTACCT-GACCGAAAAAAAATACTCCCCGTGCGCTTGGG3'

Oligomer F (SEQ ID NO:11):

5'TTATTCTTTACGACGCAGACGTTCCTG-CAGGTTGGTGGACAGGGAGAAGGAACG-CATGATTT CAGCACGAACAACTTCCCAAGCG-CACGGGGAGTATTTTTTTTCGGTCAGG3'

PCR I for Fragment I: oligodeoxynucleotide B as template, oligodeoxynucleotide A and C as primers, synthesized 280 bp Fragment I.

| PCR I mixture | (units: μl) |
|---|---|
| sterilized distilled water | 39 |
| 10 × Pfu buffer (Stratagen American Ltd.) | 5 |
| dNTP mixture (dNTP concentration 2.5 mmol/L) | 2 |
| Oligomer A primer (25 μmol/L) | 1 |
| Oligomer C primer (25 μmol/L) | 1 |
| Oligomer B template (1 μmol/L) | 1 |
| Pfu DNA polymerase (Stratagen American Ltd.) (25 U/μl) | 1 |
| Total volume | 50 μl |

PCR cycle: 95 I
2 m→(95° C. 45 s→65° C. 1 m→72° C. 1 m) × 25 cycle→72° C. 10 m→ '4° C.

PCR II for Fragment II: oligodeoxynucleotide E as template, oligodeoxynucleotide D and F as primers, synthesized 268 bp Fragment II.

| PCR II mixture | (units: μl) |
|---|---|
| sterilized distilled water | 39 |
| 10 × Pfu buffer (Stratagen American Ltd.) | 5 |
| dNTP mixture (dNTP concentration 2.5 mmol/L) | 2 |
| Oligomer D primer (25 μmol/L) | 1 |
| Oligomer F primer (25 μmol/L) | 1 |
| Oligomer E template (1 μmol/L) | 1 |
| Pfu DNA polymerase (Stratagen American Ltd.) (25 U/μl) | 1 |
| Total volume | 50 μl |

PCR cycle: the same as PCR I

Assembling of rSIFN-co cDNA

Fragment I and II were assembled together to get the complete cDNA molecular sequence of rSIFN-co using the overlapping and extending PCR method. Restriction enzyme Nde I and Pst I were introduced to clone rSIFN-co cDNA sequence into plasmid.

(1) Chemical Synthesis Primers

Oligomer G: 5'ATCGGCCATATGTGCGACCTGCCGCAGACCC3' (SEQ ID NO:12):

Oligomer H: 5'ACTGCCAGGCTGCAGTTATTCTTTACGACGCAGACGTTCC3' (SEQ ID NO:13)

(2) Overlapping and Extending PCR

| PCR mixture | (units: μl) |
|---|---|
| sterilized distilled water | 38 |
| 10 × Pfu buffer (Stratagen American Ltd.) | 5 |
| dNTP mixture (dNTP concentration 2.5 mmol/L) | 2 |
| primer G (25 μmol/L) | 1 |
| primer H (25 μmol/L) | 1 |
| *fragment I preduction (1 μmol/L) | 1 |
| *fragment II preduction (1 μmol/L) | 1 |
| Pfu DNA polymerase (Stratagen American Ltd.) (2.5 U/μl) | 1 |
| Total volume | 50μ |

*Separate and purify PCR production with StrataPrep PCR purification kit produced by Stratagen American Ltd. And dissolve into sterilized distilled water.
PCR cycle: the same as PCR I rSIFN-co Gene Clone and Sequence Analysis pLac T7 plasmid as cloning vector. pLac T7 plasmid is reconstructed with pBluescript II KS(+) plasmid produced by Stratagen (FIG. 3).

Purified PCR production of rSIFN-co cDNA with StrataPrep PCR purification kit. Digest cDNA and pLac T7 plasmid with NdeI and PstI. Run 1% agarose gel electrophoresis and separate these double-digested DNA fragments. Recover 507 bp long rSIFN-co DNA fragment and 2.9 kb plasmid DNA fragment. Ligate these fragments by T4 DNA ligase to form a recombinant plasmid. Transform $DH_{5\alpha}$ competent cells (Gibco) with the recombinant plasmid, culture at 37° C. overnight. Identify the positive recombinant colony, named pHY-1.

Run DNA sequencing with SequiTherm™ Cycle Sequencing Kit produced by American Epicentre Technologies Ltd using L1-COR Model 4000L. Primers are T7 and T3 common sequence primer, the DNA sequencing result matches theoretic design.

Purify the rSIFN-co, sequence the N-terminus amino acids, the N-terminus amino acid sequence matches experimental design which is as follows:

N-Cys-Asp-Leu-Pro-Gln-Thr-His-Ser-Leu-Gly-Asn-Arg-Arg-Ala-Leu- (SEQ ID NO: 14)

Construction, Transformation, Identification, and Hereditary Stability of Expression Vector Construction and Transformation of Expression Vector Digested E. Coli. expression vector pHY-4 (see FIG. 3) with Nde I to linearize and subsequently digest with Xba I. Run 1% agarose gel electrophoresis, and purify the 4.8 kb pHY-4 Nde I-Xba I digest fragment with QIAEX II kit produced by QIAGEN Germany Ltd.

At the same time, the pHY-4 plasmid is double digested with Nde I-Xba I. Run 1% agarose gel electrophoresis and purify the 715 bp fragment. Ligate the rSIFN-co and pHY-4 fragments with T4 DNA ligase to construct the recombinant plasmid (See FIG. 4). Transform $DH_{5\alpha}$ competent cells with the recombinant plasmid. Spread the transformed cells on LB plate with Amp, 37° C. culture overnight.

Positive Cloning Strain Screening

Randomly choose E. Coli. colonies from above LB-plate, screening the positive strains containing recombinant vector by endonuclease digesting and PCR analysis. Name one of the positive recombinant plasmid pHY-5, and name the strain containing pHY-5 plasmid PVIII. Amplify and store the positive strain with glycerol in −80° C.

High Expression of rSIFN-co Gene in E. Coli.

In pHY-5 plasmid, rSIFN-co gene is under control of strong promoter $P_{BAD}$. This promoter is positively and negatively regulated by the product of the gene araC. AraC is a transcriptional regulator that forms a complex with arabinose. In the absence of arabinose, the AraC dimer binds $O_2$ and $I_1$ forming a 210 bp loop. This conformation leads to a complete inhibition of transcription. In the presence of arabinose, the dimer is released from $O_2$ and binds $I_1$ and $I_2$ leading to transcription. Arabinose binding deactivates, represses and even activates the transcription of $P_{BAD}$ promoter, which stimulates $P_{BAD}$ inducing high expression of rSIFN-co. rSIFN-co expression level in PVIII is more than 50% of the total E. Coli. protein.

SUMMARY

RSIFN-CO is a new interferon molecule artificially built according to the conservative amino acid of human α interferons. It has been proven as a effective anti-hepatitis drug. In order to get enough pure rSIFN-co protein, a stable recombinant E. Coli. strain which high expresses rSIFN-co protein was constructed.

First, according to published rSIFN-co amino acid sequence, E. Coli. codon was used to synthesize whole cDNA of rSIFN-co. This DNA fragment was sequenced and proved that the 501 bp codon sequence and TAA termination codon sequence are valid and identical with theocratic design. Subsequent analysis revealed that the N-terminus amino acid sequence and amino acid composed of rSIFN-co produced by the recombinant strain were both identical to the prediction.

The rSIFN-co cDNA was cloned into E. Coli. high-expression vector pHY-4 plasmid to construct the recombinant plasmid pHY-5. E. Coli. LMG194 strain was further transformed with pHY-4 plasmid to get stable rSIFN-co high-expression transformant. This transformant was cultured for 30 generations. The heredity of pHY-5 recombinant plasmid in E. Coli. LMG194 was normal and stable, and the expression of rSIFN-co was high and steady.

E. Coli. LMG194, which contains recombinant pHY-5 plasmid, is actually an ideal high-expression engineering strain.

REFERENCES

1. Blatt L M, Davis J M, Klein S B. et al. The biologic activity and molecular characterization of a novel synthetic interferon-alpha species, consensus interferon. Journal of Interferon and Cytokine Research, 1996; 16(7):489-499.
2. Alton, K. et al: Production characterization and biological effects of recombinant DNA derived human IFN-α and IFN-γ analogs. In: De Maeger E, Schellekens H. eds. The Biology of Interferon System. 2nd ed. Amsterdam: Elsevier Science Publishers, 1983: 119-128
3. Pfeffer L M. Biologic activity of natural and synthetic type 1 interferons. Seminars in Oncology, 1997; 24 (3 suppl 9):S9-63-S9-69.
4. Ozes O N, Reiter Z, Klein S, et al. A comparison of interferon-con1 with natural recombinant interferons-(: antiviral, antiproliferative, and natural killer-inducing activities. J. Interferon Res., 1992; 12:55-59.
5. Heathcote E J L, Keeffe E B, Lee S S, et al. Re-treatment of chronic hepatitis C with consensus interferon. Hepatology, 1998; 27(4):1136-1143.
6. Klein M L, Bartley T D, Lai P H, et al. Structural characterization of recombinant consensus interferon-alpha. Journal of Chromatography, 1988; 454:205-215.
7. The Wisconsin Package, by Genetics Computer Group, Inc. Copyright 1992, Medison, Wis., USA
8. Nishimura, A et al: A rapid and highly efficient method for preparation of competent E. coli cells. Nuclei. Acids Res. 1990, 18:6169
9. All molecular cloning techniques used are from: Sambrook, J., E. F. Fritsch and T. Maniatis. Molecular Cloning: A laboratory manual, 2nd ed. CSH Laboratory Press, Cold Spring Harbour, N.Y. 1989.
10. Guzman, L. M et al: Tight regulation, modulation, and high-level express-ion by vectors containing the arabinose PBAD promoter. J. Bacteriol. 1995, 177: 4121~4130.

rSIFN-co cDNA Sequence Designed According to E. Coli. Codon Usage and Deduced rSIFN-co Amino Acid Sequence

```
           5'         11          21         31          41         51
    +1   M   C   D   L   P   Q   T   H   S   L   G   N   R   R   A   L   I   L   L   A
     1 ATGTGCGACC TGCCGCAGAC CCACTCCCTG GGTAACCGTC GTGCTCTGAT CCTGCTGGCT
       TACACGCTGG ACGGCGTCTG GGTGAGGGAC CCATTGGCAG CACGAGACTA GGACGACCGA

5'         71          81         91         101        111
    +1   Q   M   R   R   I   S   P   F   S   C   L   K   D   R   H   D   F   G   F   P
    61 CAGATGCGTC GTATCTCCCC GTTCTCCTGC CTGAAAGACC GTCACGACTT CGGTTTCCCG
       GTCTACGCAG CATAGAGGGG CAAGAGGACG GACTTTCTGG CAGTGCTGAA GCCAAAGGGC

5'         131        141         151        161         171
    +1   Q   E   E   F   D   G   N   Q   F   Q   K   A   Q   A   I   S   V   L   H   E
   121 CAGGAAGAAT TCGACGGTAA CCAGTTCCAG AAAGCTCAGG CTATCTCCGT TCTGCACGAA
       GTCCTTCTTA AGCTGCCATT GGTCAAGGTC TTTCGAGTCC GATAGAGGCA AGACGTGCTT
```

```
           5'             191         201         211         221         231
+1          M   I   Q   Q   T   F   N   L   F   S   T   K   D   S   S   A   A   W   D   E
        181 ATGATCCAGC AGACCTTCAA CCTGTTCTCC ACCAAAGACT CCTCCGCTGC TTGGGACGAA
            TACTAGGTCG TCTGGAAGTT GGACAAGAGG TGGTTTCTGA GGAGGCGACG AACCCTGCTT

5'             251         261         271         281         291
+1          S   L   L   E   K   F   Y   T   E   L   Y   Q   Q   L   N   D   L   E   A   C
        241 TCCCTGCTGG AAAAATTCTA CACCGAACTG TACCAGCAGC TGAACGACCT GGAAGCTTGC
            AGGGACGACC TTTTTAAGAT GTGGCTTGAC ATGGTCGTCG ACTTGCTGGA CCTTCGAACG

5'             311         321         331         341         351
+1          V   I   Q       E V G V   E   E   T   P   L   M   N   V   D   S   I   L   A
        301 GTTATCCAGG AAGTTGGTGT TGAAGAAACC CCGCTGATGA ACGTTGACTC CATCCTGGCT
            CAATAGGTCC TTCAACCACA ACTTCTTTGG GGCGACTACT TGCAACTGAG GTAGGACCGA

5'             371         381         391         401         411
+1          V   K   K   Y   F   Q   R   I   T   L   Y   L   T   E   K   K   Y   S   P   C
        361 GTTAAAAAAT ACTTCCAGCG TATCACCCTG TACCTGACCG AAAAAAAATA CTCCCCGTGC
            CAATTTTTTA TGAAGGTCGC ATAGTGGGAC ATGGACTGGC TTTTTTTTAT GAGGGGCACG
           5' 431 441 451 461 471
+1          A   W   E   V   V   R   A   E   I   M   R   S   F   S   L   S   T   N   L   Q
        421 GCTTGGGAAG TTGTTCGTGC TGAAATCATG CGTTCCTTCT CCCTGTCCAC CAACCTGCAG
            CGAACCCTTC AACAAGCACG ACTTTAGTAC GCAAGGAAGA GGGACAGGTG GTTGGACGTC
           5'             491         501
+1          E   R   L   R   R   K   E     #   (SEQ ID NO: 2)
        481 GAACGTCTGC GTCGTAAAGA ATAA
            CTTGCAGACG CAGCATTTCT TATT
```

Example 2

Separation and Purification of rSIFN-co

1. Fermentation

Inoculate the recombinant strain in LB media, shaking (200 rpm) under 37° C. overnight (approximate 18 h), then add 30% glycerol to the fermentation broth to get final concentration of 15%, allotted to 1 ml tube and kept in −20° C. as seed for production.

Add 1% of the seed to LB media, shaking (200 rpm) under 37° C. overnight to enlarge the scale of the seed, then add to RM media with a ratio of 10%, culturing under 37° C. Add arabinose (20% solution) to 0.02% as an inductor when the OD600 reaches about 2.0. 4 hours after that, stop the culture process, collect the bacteria by centrifuge, resuspend the pellet with buffer A, and keep in −20° C. overnight. Thaw and break the bacteria by homogenizer, then centrifuge. Wash the pellet with buffer B, buffer C, and distilled water to get a relatively pure inclusion body.

2. Denaturation and Renaturation

Dissolve the inclusion body in Guanidine-HCl (or urea) of 6 mol/L. The solution will be a little cloudy. Centrifuge it at a speed of 10000 rpm. Determine the protein concentration of the supernatant. This supernatant is called "denaturation solution." Add the denaturation solution to renaturation buffer, and keep the final protein concentration under 0.3 mg/ml. It is better to add the totally denaturation solution in three steps instead of one step. Keep the solution overnight under 4° C. Afterwards, dialyze 10 mol/L, 5 mol/L PB buffer and distilled water, then adjust its pH by 2 mol/L HAc-NaAc. Let it stand, then filtrate.

3. Purification

PROS HS/M Anion Exchange Chromatography:

Equivalent column with 20 mmol/L HAc—NaAc (pH 5.0)

↓

Load samples at a speed of 30 ml/min

↓

Wash with 20 CV 20 mmol/L HAc—NaAc (pH 5.0)

↓

5 CV of 0.15 mol/L NaCl + 20 mmol/L HAc—NaAc (pH 5.0) wash

↓

3 CV of 0.18 mol/L NaCl + 20 mmol/L HAc—NaAc (pH 5.0) wash

↓

0.25 mol/L NaCl + 20 mmol/L HAc—NaAc (pH 5.0) elute target protein

Chelating Sepharose™ fast flow: Add PB buffer of 0.2 mol/L (pH 6.6) and NaCl of 4 mol/L in the solution from HS to adjust solution pH to pH 6.0 and NaCl concentration to 1 mol/L.

Column with buffer D

↓

Loading at a rate of 1 ml/min

↓

Wash with buffer E

↓

Wash with buffer F

↓

Elute with buffer G

Condense the eluted solution by POROS HS/M. Sometimes a purification by sephacryl S-100 step can be added to meet stricter purity requirements.

Note:

Buffer A: 100 mmol/L Tris-HCl, pH 7.5-10 mmol/L EDTA-100 mmol/L NaCl

Buffer B: 50 mmol/L Tris-HCl, pH 7.5-1 mol/L Urea-10 mmol/L EDTA-0.5% Triton X-100

Buffer C: 50 mmol/L Tris-HCl, pH 7.5-2 mol/L Urea-10 mmol/L EDTA-0.5% Triton X-100

Buffer D: 1 mol/L NaCl—50 mmol/L $Na_2HPO_4$ (pH 5.5)

Buffer E: 1 mol/L NaCl—50 mmol/L $Na_2HPO_4$ (pH 5.0)

Buffer F: 1 mol/L NaCl—50 mmol/L $Na_2HPO_4$ (pH 4.0)

Buffer G: 1 mol/L NaCl—50 mmol/L $Na_2HPO_4$ (pH 3.6)

Renaturation buffer: 0.5 mol/L Arginine-150 mmol/L Tris-HCl, pH 7.5-0.2 mmol/L EDTA

| | |
|---|---|
| LB Media: | 1 L |
| Tryptone | 10 g |
| Yeast extracts | 5 g |
| NaCl | 10 g |

| | |
|---|---|
| RM Media: | 1 L |
| Casein | 20 g |
| MgCl | 1 mmol/L (0.203 g) |
| $Na_2HPO_4$ | 4 g; |
| $KH_2PO_4$ | 3 g, |
| NaCl | 0.5 g |
| $NH_4Cl$ | 1 g |

After purification, the buffer was changed to PBS (pH 7.0) along with the step of condensing by POROS HS/M. This is called the "Protein Stock Solution." It can directly used in the preparation of injections or sprays, or stored at 2-8° C.

Formula for Injection:

| | Solution | Lyophilized powder |
|---|---|---|
| Solution of rSIFN-co | 34.5 μg/ml | 34.5 μg/ml |
| PB (pH 7.0) | 25 mmol/L | 10 mmol/L |
| Glycine | — | 0.4 mol/L |
| NaCl | 0.1 mol/L | — |

For Spray:

| | |
|---|---|
| EDTA | 0.01% |
| Tween 80 | 0.05% |
| Trisodium citrate | 10 mmol/L |
| Glycerol | 1.26% |
| Sodium Chloride | 0.03% |
| Phenylmethanol | 0.5% |
| HSA | 0.1% |
| rSIFN-co | 10 μg/ml |

Quality Control Process

During purification tests for protein content, protein purity, specific activity and pyrogen are conducted after each step. When the stock solution is obtained, all the tests listed in the table are done one after the other.

The quality of the product is controlled according to "Chinese Requirements for Biologics"

1. Original Protein Solution

| Lowry | |
|---|---|
| Item of Test | Method |
| Protein Stock Solution: | |
| Test for Protein Content | Lowry |
| Test for Protein Purity | Non-reductive SDS-PAGE (sodium dodecyl sulfate polyacrylamide gel electrophoresis) |
| | HPLC Analysis |
| Test for Molecular Weights | Reductive SDS-PAGE |
| Test for Specific Activity | According to Method in "Specific Activity Test of Interferon |
| Test for Leftover Exogenetic DNA | Using DNA Labeling and Detection Kit |
| Test for Activity of Leftover Antibiotics | According to Method in "Chemical and Other Test Methods for Biologics" |
| Test for Bacterial Endotoxin | According to Method in "Requirements for Bacterial Endotoxin Test of Biologics" |
| Test for Isoelectronic Point | Isoelectric Focusing Electrophoresis |
| Test for Identify Characteristics of the Protein | UV spectrum (range of wavelength: 190-380 nm) |
| | Peptide Mapping (hydrolyzed by pancreatic enzyme, analyzed by C-18 column) |
| | N-terminal Sequence Test |
| | C-terminal Sequence Test |
| | Circular Dichroism |
| | Amino Acid Analysis |
| Semi-finished Product | |
| Test for Bacterial Endotoxin | According to Method in "Requirements for Bacterial Endotoxin Test of Biologics" |
| Product | |
| Appearance Check | |
| Chemical | According to Method in "Chemical and Other Test Methods for Biologics" |
| Test for Specific Activity | According to Method in "Specific Activity Test of Interferon |
| Sterility Test | According to Method in "c" |
| Abnormal Toxicity Test | Test on Mouse |
| Pyrogen Test | According to Method in "Requirements for Pyrogen Test of Biologics" |
| Test for Stability of Product | |

Note:
"Chemical and Other Test Methods for Biologics", "Requirements for Pyrogen Test of Biologics" and "Requirements for Bacterial Endotoxin Test of Biologics" all can be found in the "Chinese Requirements for Biologics." "Chinese Requirements for Biologics," PAN Zhengan, ZHANG Xinhui, DUAN Zhibing, et al. Chinese Biologics Standardization committee. Published by Chemical Industry Publishing Company, 2000.

Example 3

Stability of lyophilized Powder of Recombinant Super-Compound Interferon Injection The stability experiments were carried out with samples of lyophilized powder of recombinant super-compound interferon (rSIFN-co) injection in two specifications and three batches. The experiments started on April, 2000.

1. Sample Source

Samples were supplied by Sichuan Huiyang Life-engineering Ltd., Sichuan Province. Lot: 990101-03, 990101-05, 990102-03, 990102-05, 990103-03, 990103-05

2. Sample Specifications

Every sample in this experiment should conform with the requirements in the table below.

TABLE 1

Standard of Samples in Experiment

| Items | Standards |
|---|---|
| 1. Appearance | white loose powder |
| 2. Dissolving time | dissolve rapidly in injection water(within 2 min) at room temperature |
| 3. Clarity | colorless liquid or with little milk-like glisten; should not be cloudy, impurity or with indiscernible deposit |
| 4. pH value | 6.5~7.5 |
| 5. Potency (IU/dose) | 80%~150% of indicated quantity (9 μg: 4.5 × $10^6$ IU, 15 μg: 7.5 × $10^6$ IU) |
| 6. Moisture | no more than 3.0% (W/W) |

3. Experiment Content 15.3.1 Test samples at 2~8° C.: The test samples were put into a 2-8° C. refrigerator, then the above items of these samples were respectively tested in the $1^{st}$, $3^{rd}$, $6^{th}$, $9^{th}$, $12^{th}$, $18^{th}$, $24^{th}$, $30^{th}$, $36^{th}$ month. The results were recorded. 15.3.2 Test samples at 25° C.: The test samples were put into a thermostat at 25° C., then the above items of these samples were respectively tested in the $1^{st}$, $3^{rd}$, $6^{th}$, $9^{th}$, $12^{th}$, $18^{th}$, $24^{th}$, $30^{th}$ month. The results were recorded.

15.3.3 Test samples at 37° C.: The test samples were put into a thermostat at 37° C., then the above items of these samples were respectively tested in the $1^{st}$, $3^{rd}$, $6^{th}$, $9^{th}$, $12^{th}$, $18^{th}$, $24^{th}$ month. The results were recorded.

4. Results and Conclusion

1) At 37° C., according to data collected at designated points during testing and compared with data before testing, the potency began descending from the $6^{th}$ month and the changes in the three batches were similar. The appearance of other items had no changes.

2) At 25° C., according to data collected at designated points during testing and compared with data before the testing, the potency only had a little change, and the changes in the three batches were similar. The appearance of other items had no changes.

3). At 2-8° C., according to data collected at designated points during testing and compared with data before testing, the potency of the three batches all were stable. The appearance of other items also had no changes.

In conclusion, it is suggested that the lyophilized powder of recombinant super-compound interferon for injection should be better stored and transported at low temperatures. Without such conditions, the product can also be stored for short periods (i.e. 3 months) at room temperature.

Example 4 rSIFN-co Inhibits HBV-DNA Duplication and Secretion of HBsAg and HBeAg

Materials

Solvent and Dispensing Method: Add 1 ml saline into each vial, dissolve, and mix with MEM culture medium at different concentrations. Mix on the spot.

Control drugs: IFN-α2b (Intron A) as lyophilized powder, purchased from Schering Plough. $3 \times 10^6$ U each, mix to $3 \times 10^6$ IU/ml with culture medium; Infergen® (liquid solution), purchased from Amgen, gig, 0.3 ml each, equal to $9 \times 10^6$ IU, and mix with $9 \times 10^6$ IU/ml culture medium preserve at 4° C.; 2.2.15 cell: 2.2.15 cell line of hepatoma (Hep G2) cloned and transfected by HBV DNA, constructed by Mount Sinai Medical Center.

Reagent: MEM powder, Gibco American Ltd. cattle fetal blood serum, HycloneLab American Ltd. G-418 (Geneticin); MEM dispensing, Gibco American Ltd.; L-Glutamyl, imported and packaged by JING KE Chemical Ltd.; HBsAg and HBeAg solid-phase radioimmunoassay box, Northward Reagent Institute of Chinese Isotope Ltd.; Biograncetina, Northern China Medicine; And Lipofectin, Gibco American Ltd.

Experimental goods and equipment: culture bottle, Denmark Tunclon™; 24-well and 96-well culture board, Corning American Ltd.; Carbon Dioxide hatching box, Shel-Lab American Ltd.; MEM culture medium 100 ml:10% cattle fetal blood serum, 3% Glutamyl 1%, G418 380 μg/ml, biograncetina 50 U/ml.

Method:

2.2.15 cell culture: Added 0.25% pancreatic enzyme into culture box with full of 2.2.15 cell, digest at 37° C. for 3 minutes, and add culture medium to stop digest and disturb it to disperse the cells, reproduce with ratio of 1:3. They will reach full growth in 10 days.

Toxicity test: Set groups of different concentrations and a control group in which cell is not acted on with medicine. Digest cell, and dispense to a 100,000 cell/ml solution. Inoculate to 96-well culture board, 200 μl each well, culture at 37° C. for 24 h with 5% $CO_2$. Test when simple cell layer grows.

Dispense rSIFN-co to $1.8 \times 10^7$ IU/ml solution than prepare a series of solutions diluted at two-fold gradients. Add into 96-well culture board, 3 wells per concentration. Change the solution every 4 days. Test cytopathic effect by microscope after 8 days. Fully destroy as 4, 75% as 3, 50% as 2, 25% as 1, zero as O. Calculate average cell lesion and inhibition rate of different concentrations. Calculate TC50 and TC0 according to the Reed Muench method.

$$TC50 = \text{Antilog}\left(B + \frac{50 - B}{A - B} \times C\right)$$

A=log>50% medicine concentration, B=log<50% medicine concentration, C=log dilution power Inhibition test for HBeAg and HBsAg: Separate into positive and negative HBeAg and HBsAg contrast groups, cell contrast group and medicine concentration groups. Inoculate 700,000 cells/ml of 2.2.15 cell into 6-well culture board, 3 ml each well, culture at 37° C. for 24 h with 5% $CO_2$, then prepare 5 gradiently diluted solutions with 3-fold as the grade (Prepare 5 solutions, each with a different protein concentration. The concentration of Solution 2 is 3 times lower than that of Solution 1, the concentration of Solution 3 is 3 times lower than that of Solution 2, etc.) $4.5 \times 10^6$ IU/ml, $1.5 \times 10^6$ IU/ml, $0.5 \times 10^6$ IU/ml, $0.17 \times 10^6$ 1 U/ml, and $0.056 \times 10^6$ IU/ml, 1 well per concentration, culture at 37° C. for 24 h with 5% $CO_2$. Change solutions every 4 days using the same solution. Collect all culture medium on the $8^{th}$ day. Preserve at −20° C. Repeat test 3 times to estimate HBsAg and HBeAg with solid-phase radioimmunoassay box (Northward Reagent Institute of Chinese Isotope Ltd.). Estimate cpm value of each well with a γ-accounting machine.

Effects calculation: Calculate cpm mean value of contrast groups and different-concentration groups and their standard deviation, P/N value such as inhibition rate, IC50 and SI.

1)

$$\text{Antigen inhibition rate (\%)} = \frac{A-B}{A} \times 100$$

A=cpm of control group; B=cpm of test group;

2) Counting the half-efficiency concentration of the medicine $$\text{Antigen inhibition } IC50 = \text{Antilog}\left(B + \frac{50-B}{A-B} \times C\right)$$

A=log>50% medicine concentration, B=log<50% medicine concentration, C=log dilution power 3) SI of interspace-conformation changed rSIFN-co effect on HBsAg and HBeAg in 2.2.15 cell culture:

$$SI = \frac{TC50}{IC50}$$

4) Estimate the differences in cpm of each dilution degree from the control group using student t test Southern blot: (1) HBV-DNA extract in 2.2.15 cell: Culture cell 8 days. Exsuction culture medium (Separate cells from culture medium by means of draining the culture medium.). Add lysis buffer to break cells, then extract 2 times with a mixture of phenol, chloroform and isoamyl alcohol (1:1:1), 10,000 g centrifuge. Collect the supernatant adding anhydrous alcohol to deposit nucleic acid. Vacuum draw, re-dissolve into 20 μl TE buffer. (2) Electrophoresis: Add 6×DNA loading buffer, electrophoresis on 1.5% agarose gel, IV/cm, at fixed pressure for 14-18 h. (3) Denaturation and hybridization: respectively dip gel into HCl, denaturation buffer and neutralization buffer. (4) Transmembrane: Make an orderly transfer of DNA to Hybond-N membrane. Bake, hybridize and expose with dot blot hybridization. Scan and analyze relative density with gel-pro software. Calculate inhibition rate and IC50.

Results

Results from Tables 1, 2 and 3 show: After maximum innocuous concentration exponent culturing for 8 days with 2.2.15 cell, the maxima is $9.0\pm0\times10^6$ IU/ml average inhibition rate of maximum innocuous concentration rSIFN-co to HBeAg is $46.0\pm5.25\%$ (P<O·001), IC50 is $4.54\pm1.32\times10^6$ IU/ml, SI is 3.96; rate to HBsAg is 44.8±6.6%, IC50 is $6.49\pm0.42\times10^6$ IU/ml, SI is 2.77. This shows that rSIFN-co can significantly inhibit the activity of HBeAg and HBsAg, but that the IFN of the contrast group and Infergen® cannot. It has also been proved in clinic that rSIFN-co can decrease HBeAg and HBsAg or return them to normal levels.

TABLE 1

Results of inhibition rate of rSIFN-co to HBsAg and HBeAg

| Concentration ($\times 10^4$ IU/ml) | First well | Second well | Third well | Inhibition rate First well | Inhibition rate Second well | Inhibition rate Third rate | Average inhibition rate | Accumulation |
|---|---|---|---|---|---|---|---|---|
| | | | | First batch: (rSIFN-co) Inhibition effect to HBeAg | | | | |
| 900 | 9026 | 8976 | 10476 | 0.436227 | 0.43935 | 0.345659 | 0.407079 | 0.945909 |
| 300 | 9616 | 12082 | 10098 | 0.3993754 | 0.245347 | 0.369269 | 0.337997 | 0.5388299 |
| 100 | 9822 | 16002 | 12800 | 0.386508 | 0.0005 | 0.2005 | 0.195836 | 0.200833 |
| 33.33333 | 15770 | 19306 | 16824 | 0.014991 | 0 | 0 | 0.004997 | 0.0049969 |
| 11.11111 | 19172 | 22270 | 18934 | 0 | 0 | 0 | 0 | 0 |
| Control | Cell 16010 | | | Blank 0 | | | Dilution 3 | |
| | | | | Inhibition effect to HBsAg | | | | |
| 900 | 7706 | 7240 | 7114 | 0.342155 | 0.381936 | 0.392693 | 0.372261 | 0.922258 |
| 300 | 8856 | 7778 | 9476 | 0.2439816 | 0.336008 | 0.191053 | 0.257014 | 0.5499972 |
| 100 | 10818 | 10720 | 10330 | 0.07649 | 0.084856 | 0.118149 | 0.093165 | 0.292983 |
| 33.33333 | 10744 | 11114 | 10570 | 0.082807 | 0.051221 | 0.097661 | 0.07723 | 0.1998179 |
| 11.11111 | 10672 | 9352 | 10810 | 0.088953 | 0.201639 | 0.077173 | 0.122588 | 0.122588 |
| Control | Cell 11714 | | | Blank 0 | | | Dilution 3 | |
| | | | | Second batch: (rSIFN-co) Inhibition effect to HBeAg | | | | |
| 900 | 7818 | 8516 | 9350 | 0.554378 | 0.514592 | 0.467054 | 0.512008 | 1.371181 |
| 300 | 10344 | 10628 | 9160 | 0.4103967 | 0.394209 | 0.477884 | 0.427497 | 0.8591731 |
| 100 | 12296 | 14228 | 13262 | 0.299134 | 0.18901 | 0.244072 | 0.244072 | 0.4316522 |
| 33.33333 | 15364 | 17414 | 16188 | 0.124259 | 0.00741 | 0.77291 | 0.069653 | 0.1876045 |
| 11.11111 | 17386 | 13632 | 15406 | 0.009006 | 0.222982 | 0.121865 | 0.117951 | 0.117951 |
| Control | Cell 16962 | | | Blank 0 | | | Dilution 3 | |
| | | | | Inhibition effect to HBsAg | | | | |
| 900 | 5784 | 6198 | 5792 | 0.498265 | 0.462353 | 0.497571 | 0.486063 | 0.893477 |
| 300 | 7150 | 8534 | 8318 | 0.379771 | 0.259715 | 0.278452 | 0.30598 | 0.4074138 |
| 100 | 9830 | 11212 | 10210 | 0.147294 | 0.027412 | 0.11433 | 0.096345 | 0.101434 |
| 33.33333 | 13942 | 12368 | 13478 | 0 | 0 | 0 | 0 | 0.0050891 |
| 11.11111 | 12418 | 11634 | 11352 | 0 | 0 | 0.015267 | 0.005089 | 0.005089 |
| Control | Cell | | | Blank 0 | | | Dilution 3 | |

TABLE 1-continued

Results of inhibition rate of rSIFN-co to HBsAg and HBeAg

Third batch: (rSIFN-co)
Inhibition effect to HBeAg

| | | | | | | | | |
|---|---|---|---|---|---|---|---|---|
| 900 | 9702 | 9614 | 8110 | 0.428016 | 0.433204 | 0.521872 | 0.461031 | 1.316983 |
| 300 | 8914 | 10032 | 8870 | 0.4744723 | 0.40856 | 0.477066 | 0.453366 | 0.8559525 |
| 100 | 16312 | 12688 | 13934 | 0.038321 | 0.251975 | 0.178517 | 0.156271 | 0.402586 |
| 33.33333 | 15080 | 12814 | 13288 | 0.110954 | 0.244547 | 0.216602 | 0.190701 | 0.2463153 |
| 11.11111 | 21928 | 15366 | 15728 | 0 | 0.094093 | 0.072751 | 0.0055615 | 0.055615 |
| Control | | Cell 17544 | | | Blank 0 | | | Dilution 3 |

Inhibition effect to HBsAg

| | | | | | | | | |
|---|---|---|---|---|---|---|---|---|
| 900 | 5616 | 6228 | 5346 | 0.496864 | 0.442035 | 0.521054 | 0.486651 | 0.763125 |
| 300 | 8542 | 8590 | 7096 | 0.234725 | 0.230425 | 0.364272 | 0.276474 | 0.2764738 |
| 100 | 11420 | 11360 | 11394 | 0 | 0 | 0 | 0 | 0 |
| 33.33333 | 12656 | 11582 | 13110 | 0 | 0 | 0 | 0 | 0 |
| 11.11111 | 13142 | 12336 | 13342 | 0 | 0 | 0 | 0 | 0 |
| Control | | Cell 11528 | | | Blank 0 | | | Dilution 3 |

Results of inhibition rate of rSIFN-co to HBsAg and HBeAg

| Concentration ($\times 10^4$ IU/ml) | 1-Accumulation | Accumulated inhibition rate |
|---|---|---|
| First batch: (rSIFN0-co) Inhibition effect to HBeAg | | |
| 900 | 0.592921 | 0.614693546 |
| 300 | 1.254924 | 0.300392321 |
| 100 | 2.059088 | 0.08867188 |
| 33.33333 | 3.054091 | 0.001633453 |
| 11.11111 | 4.054091 | 0 |
| Control | IC50 602.74446016 | |
| Inhibition effect to HBsAg | | |
| 900 | 0.627739 | 0.595006426 |
| 300 | 1.370724 | 0.286349225 |
| 100 | 2.27756 | 0.113977019 |
| 33.33333 | 3.20033 | 0.058767408 |
| 11.11111 | 4.077742 | 0.02918541 |
| Control | IC50 641.7736749 | |
| Second batch: (rSIFN-co) Inhibition effect to HBeAg | | |
| 900 | 0.487992 | 0.737521972 |
| 300 | 1.060496 | 0.447563245 |
| 100 | 1.816423 | 0.19201839 |
| 33.33333 | 2.74677 | 0.063933386 |
| 11.11111 | 3.628819 | 0.03148073 |
| Control | IC50 365.9357846 | |
| Inhibition effect to HBsAg | | |
| 900 | 0.513937 | 0.634835847 |
| 300 | 1.207957 | 0.252210647 |
| 100 | 2.111612 | 0.04583464 |
| 33.33333 | 3.111612 | 0.001632835 |
| 11.11111 | 4.106523 | 0.001237728 |
| Control | IC50 611.0919568 | |
| Third batch: (rSIFN-co) Inhibition effect to HBeAg | | |
| 900 | 0.538969 | 0.709599543 |
| 300 | 1.085603 | 0.440859127 |
| 100 | 1.929332 | 0.172641621 |
| 33.33333 | 2.738631 | 0.082519158 |
| 11.11111 | 3.683017 | 0.014875633 |
| Control | IC50 382.0496935 | |
| Inhibition effect to HBsAg | | |
| 900 | 0.513349 | 0.597838293 |
| 300 | 1.236875 | 0.182690031 |
| 100 | 2.236875 | 0 |
| 33.33333 | | 0 |
| 11.11111 | 4.236875 | 0 |
| Control | IC50 694.7027149 | |

HBeAg: Average IC50: 450.2434 SD: 132.315479
HBsAg: Average IC50: 649.1894 SD: 42.29580

TABLE 2

Results of inhibition rate of Intron A (IFN-α2b) to HBsAg and HBeAg

| Concentration (×10⁴IU/ml) | First well | Second well | Third well | Inhibition rate First well | Inhibition rate Second well | Inhibition rate Third well | Average inhibition rate | Accumulation | 1-Accumulation | Accumulated inhibition rate |
|---|---|---|---|---|---|---|---|---|---|---|
| | | | | | | | | | | |
| | | | | | Inhibition effect to HBeAg | | | | | |
| 300 | 14918 | 11724 | 9950 | 0 | 0.029711 | 0.176529 | 0.068747 | 0.068747 | 0.931253 | 0.068746724 |
| 100 | 14868 | 16890 | 15182 | 0 | 0 | 0 | 0 | 0 | 1.931253 | 0 |
| 33.33333 | 16760 | 21716 | 16400 | 0 | 0 | 0 | 0 | 0 | 2.931253 | 0 |
| 11.11111 | 20854 | 15042 | 16168 | 0 | 0 | 0 | 0 | 0 | 3.931253 | 0 |
| 3.703704 | 12083 | 12083 | 12083 | 0 | 0 | 0 | 0 | 0 | 4.931253 | 0 |
| Control | Cell 17544 | | | Blank 0 | | | Dilution 3 | | IC50 FALSE | |
| | | | | | Inhibition effect to HBsAg | | | | | |
| 300 | 9226 | 8196 | 9658 | 0.152489 | 0.247106 | 0.521054 | 0.1708 | 0.189295 | 0.8292 | 0.185857736 |
| 100 | 10946 | 10340 | 10828 | 0 | 0.050156 | 0.364272 | 0.018495 | 0.0184947 | 1.810705 | 0.010110817 |
| 33.33333 | 12250 | 12980 | 13934 | 0 | 0 | 0 | 0 | 0 | 2.810705 | 0 |
| 11.11111 | 12634 | 12342 | 12000 | 0 | 0 | 0 | 0 | 0 | 3.810705 | 0 |
| 3.703704 | 10886 | 10886 | 10886 | 0 | 0 | 0 | 0 | 0 | 4.810705 | 0 |
| Control | Cell 10886 | | | Blank 0 | | | Dilution 3 | | IC50 FALSE | |

TABLE 3

Results of inhibition rate of Infergen ® to HBsAg and HBeAg

| Concentration (×10⁴IU/ml) | First well | Second well | Third well | Inhibition rate First well | Inhibition rate Second well | Inhibition rate Third well | Average inhibition rate | Accumulation | 1-Accumulation | Accumulated inhibition rate |
|---|---|---|---|---|---|---|---|---|---|---|
| | | | | First batch: (Infergen ®) Inhibition effect to HBeAg | | | | | | |
| 900 | 14172 | 12156 | 17306 | 0.091655 | 0.2208690 | 0 | 0.104175 | 0.306157 | 0.895825 | 0.254710274 |
| 300 | 13390 | 12288 | 16252 | 0.1417767 | 0.2124090 | 0 | 0.118062 | 0.2019827 | 1.777764 | 0.102024519 |
| 100 | 14364 | 18834 | 14194 | 0.079349 | 0 | 0.090245 | 0.056531 | 0.083921 | 2.721232 | 0.029916678 |
| 33.33333 | 15722 | 16034 | 16340 | 0 | 0 | 0 | 0 | 0.0273897 | 3.721232 | 0.007306592 |
| 11.11111 | 17504 | 17652 | 14320 | 0 | 0 | 0.082169 | 0.02739 | 0.02739 | 4.693843 | 0.005801377 |
| Control | Cell 15602 | | | Blank 0 | | | Dilution 3 | | IC50 FALSE | |
| | | | | Inhibition effect to HBsAg | | | | | | |
| 900 | 12080 | 11692 | 12234 | 0 | 0.01275 | 0 | 0.00425 | 0.025163 | 0.99575 | 0.024647111 |
| 300 | 12840 | 11484 | 12350 | 0 | 0.030313 | 0 | 0.010104 | 0.0209125 | 1.985646 | 0.010422073 |
| 100 | 12894 | 14696 | 15086 | 0 | 0 | 0 | 0 | 0.010808 | 2.985646 | 0.003606955 |
| 33.33333 | 15032 | 12928 | 13020 | 0 | 0 | 0 | 0 | 0.0108081 | 3.985646 | 0.002704416 |
| 11.11111 | 11794 | 11984 | 11508 | 0.004137 | 0 | 0.028287 | 0.010808 | 0.010808 | 4.974837 | 0.002167838 |
| Control | Cell 11843 | | | Blank 0 | | | Dilution 3 | | IC50 FALSE | |
| | | | | Second batch: (Infergen ®) Inhibition effect to HBeAg | | | | | | |
| 900 | 6278 | 6376 | 6408 | 0.200051 | 0.187564 | 0.183486 | 0.190367 | 0.274635 | 0.809633 | 0.253290505 |
| 300 | 7692 | 9092 | 6394 | 0.0198777 | 0 | 0.18527 | 0.068383 | 0.0842678 | 1.74125 | 0.046161005 |
| 100 | 8960 | 7474 | 8190 | 0 | 0.0476550 | 0 | 0.015885 | 0.015885 | 2.725365 | 0.005794856 |
| 33.33333 | 8530 | 8144 | 9682 | 0 | 0 | 0 | 0 | 0 | 3.725365 | 0 |
| 11.11111 | 7848 | 7848 | 7848 | 0 | 0 | 0 | 0 | 0 | 4.725365 | 0 |
| Control | Cell 7848 | | | Blank 0 | | | Dilution 3 | | IC50 FALSE | |
| | | | | Inhibition effect to HBsAg | | | | | | |
| 900 | 12364 | 12268 | 12274 | 0.036171 | 0.043655 | 0.043187 | 0.041004 | 0.140162 | 0.958996 | 0.12751773 |
| 300 | 11590 | 12708 | 13716 | 0.0965076 | 0.009355 | 0 | 0.035287 | 0.0991581 | 1.923706 | 0.0490186 |
| 100 | 12448 | 13468 | 13982 | 0.029623 | 0 | 0 | 0.009874 | 0.063871 | 2.913834 | 0.02144964 |
| 33.33333 | 12616 | 11346 | 12444 | 0.016526 | 0.115529 | 0.029935 | 0.053996 | 0.0539965 | 3.859838 | 0.013796309 |
| 11.11111 | 12828 | 12828 | 12828 | 0 | 0 | 0 | 0 | 0 | 4.859838 | 0 |
| Control | Cell 12828 | | | Blank 0 | | | Dilution 3 | | IC50 FALSE | |
| | | | | Third batch: (Infergen ®) Inhibition effect to HBeAg | | | | | | |
| 900 | 7240 | 6642 | 6158 | 0.064599 | 0.14186 | 0.204393 | 0.136951 | 0.217399 | 0.863049 | 0.201211735 |
| 300 | 11072 | 8786 | 6902 | 0 | 0 | 0.108269 | 0.03609 | 0.0804479 | 1.82696 | 0.042176564 |
| 100 | 7016 | 9726 | 7552 | 0.09354 | 0 | 0.024289 | 0.039276 | 0.044358 | 2.787683 | 0.015663017 |
| 33.33333 | 7622 | 8866 | 8676 | 0.015245 | 0 | 0 | 0.005082 | 0.0050818 | 3.782601 | 0.001341671 |
| 11.11111 | 7740 | 7740 | 7740 | 0 | 0 | 0 | 0 | 0 | 4.782601 | 0 |
| Control | Cell 7740 | | | Blank 0 | | | Dilution 3 | | IC50 FALSE | |

TABLE 3-continued

Results of inhibition rate of Infergen ® to HBsAg and HBeAg

| Concentration (×10⁴IU/ml) | First well | Second well | Third well | Inhibition rate First well | Second well | Third well | Average inhibition rate | Accumulation | 1-Accumulation | Accumulated inhibition rate |
|---|---|---|---|---|---|---|---|---|---|---|
| Inhibition effect to HBsAg | | | | | | | | | | |
| 900 | 11048 | 11856 | 11902 | 0.04775 | 0 | 0 | 0.015917 | 0.015917 | 0.984083 | 0.015916796 |
| 300 | 13454 | 12896 | 11798 | 0 | 0 | 0 | 0 | 0 | 1.984083 | 0 |
| 100 | 12846 | 13160 | 12546 | 0 | 0 | 0 | 0 | 0 | 2.984083 | 0 |
| 33.33333 | 12680 | 12458 | 12360 | 0 | 0 | 0 | 0 | 0 | 3.984083 | 0 |
| 11.11111 | 11602 | 11602 | 11602 | 0 | 0 | 0 | 0 | 0 | 4.984083 | 0 |
| Control | Cell 11602 | | | Blank 0 | | | Dilution 3 | | | IC50 FALSE |

HBeAg: Average IC50: 0 SD: 0
HBsAg: Average IC50: 0 SD: 0

Example 5

Preparation of rSIFN-co

| Preparation of lyophilized injection | |
|---|---|
| | Lyophilized powder |
| Stock Solution of rSIFN-co | 34.5 μg/ml |
| PB (pH 7.0) | 10 mmol/L |
| Glycine | 0.4 mol/L |

Preparation technique: Weigh materials according to recipe. Dissolve with sterile and pyrogen-free water. Filter through 0.22 μm membrane to de-bacterialize, preserve at 6-10° C. Fill in vials after affirming it is sterile and pyrogen-free, 0.3 ml/vial or 0.5 ml/vial, and lyophilize in freeze dryer.

| Preparation of liquid injection | |
|---|---|
| | Solution |
| Stock Solution of rSIFN-co | 34.5 μg/ml |
| PB (pH 7.0) | 25 mmol/L |
| NaCl | 0.1 mol/L |

Preparation: Weigh materials according to recipe. Add to desired level with sterile and pyrogen-free water. Filter through 0.22 μm membrane to de-bacterialize, preserve at 6-10° C. Fill in airtight vial after affirming it is sterile and non-pyrogen at 0.3 ml/vial or 0.5 ml/vial. Storage at 2-10° C., and protect from light.

Example 6

Acute Toxicity of rSIFN-co

Treat mice with large dose (150 μg/kg, equal to 1000 times of the normal dose per kilo used in treatment of adult patients) of rSIFN-co at one time by intramuscular injection. Then, observe and record their deaths and toxic reactions. Results show that: 24 hours after injection, no abnormal reaction had been recorded. The organs of the animals which had been selected to be killed also had no signs of abnormal changes. Those remaining mice were all kept alive and were normal after two weeks. The weights of mice in the experimental group and control group all increased, and the ratio of increase had no obvious difference between the two groups (P>0.05) according to their weights on the fourteenth day. No abnormal changes were seen from the main organs of those mice after two weeks.

1. Experimental material 1.1 Animals 40 healthy adult mice, weighing 18-22 g, half male and half female, qualified by Sichuan experiment animal control center.

2.2 Medicines rSIFN-co (Provided by Sichuan Huiyang Life-engineering Ltd.) sterilized solution, 0.15 mg/ml, Lot: 981201 rSIFN-co was administered i.m. in saline.

2. Method

Separate the 40 mice into two groups randomly, one for experimental medicine, another for control. Inject medicines or saline at the same ratio (0.1 ml/10 g) through muscle to each mouse according to which group they belong. (150 μg/kg of rSIFN-co for experimental group; and saline for control group). After injection, observe and record acute toxicity shown in mice. Kill half of the mice (male and female each half) to check whether there were any abnormal pathologic changes in their main organs, such as heart, spleen, liver, lung, kidney, adrenal gland, stomach, duodenum, etc. after 24 hours. Those remains were kept and observed until the fourteenth day. Weigh all mice, kill them, and then observe the appearance of the organs listed above to see if there are any abnormalities. Take pathological tissue and examine it, using the examination to assess the difference in weight increases in the two groups.

3. Results

Results show that there was no acute toxicity seen after all mice were treated with i.m. rSIFN-co with 150 μg/kg at a time, equal to 1000 times the normal dose per kilo used in treatment of adult patients. In the 14 days after injection, all mice lived well. They ate, drank, exercised, and excreted normally and showed normal hair conditions. None of them died. The observation of the main organs of the randomly selected mice shows no abnormal changes 24 hours after injection. 14 days after injection, all remaining mice were killed. Autopsies also showed no changes. The weights of mice in the two groups all increased, but no obvious difference was shown when accessed with statistic method (p>0.05). See Table 1:

TABLE 1

Influence to weights of mice after injection of rSIFN-co

| Group | Dose | Animal | Weights before injection (g) | Weights after injection (g) | Increased value of weights (g) |
|---|---|---|---|---|---|
| Control | 0 | 20 | 19.8 ± 1.7 | 30.8 ± 2.8 | 11.0 ± 2.9 |
| rSIFN-co | 150 | 20 | 19.4 ± 1.7 | 32.1 ± 3.3 | 12.7 ± 4.3 |

3. Conclusion

Under conditions of this experiment, there were no toxic reactions in all mice after injection of rSIFN-co with 150 μg/kg. The conclusion can be reached that the maximum tolerable dose of i.m. in mice is 150 μg/kg, which is equal to 1000 times the normal dose per kilo used in treatment of adult patients.

Example 7

The Clinic Effects of Recombinant Super-Compound Interferon (rSIFN-co)

The recombinant super-compound interferon (rSIFN-co) is an invention for viral disease therapy, especially for hepatitis. Meanwhile, it can inhibit the activity of EB viruses, VSV, Herpes simplex viruses, cornaviruses, measles viruses et al. Using Wish cells/VSV system as the assay for anti-virus activity, the results showed that: the other rIFN, was $0.9 \times 10^8$ IU/mg, Intron A was $2.0 \times 10^8$ IU/mg and rSIFN-co was $9 \times 10^8$ IU/mg. The anti-viral activity of rSIFN-co is much higher than those of the former two.

Under the permission of the State Food and Drug Administration (SFDA), People's Republic of China, the clinical trials have taken place in West China Hospital, Sichuan University, the Second Hospital of Chongqing Medical University, the First Hospital of School of Medical, Zhejiang University since the February 2003. The clinical treatment which focuses on the hepatitis B is conducted under the guidance of the mutilcenter, double-blind random test. IFN-α1b was used as control, and the primary results showed the following:

The Effect of rSIFN-co Compared with IFN-α1b in the Treatment of Chronic Active Hepatitis B 1. Standard of patients selection: The standard 1-4 are effective to both treatment with rSIFN-co (9 μg) and IFN-α1b (5 MU, 50 μg), and the standard 1-5 are for rSIFN-co (15 μg) treatment.

1). Age: 18-65

2). HBsAg test positive last over six months, HBeAg test positive, PCR assay, HBV-DNA copies $\geq 10^5$/ml 3). ALT $\geq$ two times of the normal value 4). Never received IFN treatment; or those received the Lamividine treatment but failed or relapsed 5) Once received other IFNs (3 MU or 5 MU) treatment six months ago, following the standard of SFDA but failed or relapsed 2. Evaluation of the Effects:

In reference to the recommendations from the Tenth China National Committee of Virus Hepatitis and Hepatopathy, the effects were divided into three degrees according to the ALT level, HBV-DNA and HBeAg tests.

Response: ALT normal level, HBV-DNA negative, HBeAg negative

Partial response: ALT normal level, HBV-DNA or HBeAg negative

Non response: ALT, HBV-DNA and HBeAg unchanged

The response and partial response groups consider as effective cases.

3. Results of Clinic Trial:

| Period | group | Medicine | cases | Effective Rate | HBsAg Transfer to negative rate | HBeAg Transfer to negative rate | HBV-DNA Transfer to negative rate | Heptal function Recover rate |
|---|---|---|---|---|---|---|---|---|
| 8-12 week | A | rSIFN-co (9 μg) | 32 | 46.88 (15) | 9.38 (3) | 28.12 (9) | 37.50 (12) | 84.38 (27) |
| | B | IFN-α1b (5 MU, 50 μg) | 32 | 21.88 (7) | 0.00 (0) | 9.38 (3) | 15.62 (5) | 56.25 (18) |
| 16-24 week | A | rSIFN-co (9 μg) | 64 | 54.69 (35) | 7.81 (5) | 25.00 (16) | 34.38 (22) | 90.62 (58) |
| | B | IFN-α1b (5MU, 50 μg) | 64 | 25.00 (16) | 0.00 (0) | 9.38 (6) | 18.75 (12) | 78.13 (50) |

Group A: treatment with rSIFN-co (9 μg)
Group B: treatment with IFN-α1b (5MU, 50 μg)

In Group C, the cases were chronic active hepatitis B treatment with other IFNs (3 MU or 5 MU) before but failed or relapsed and treated with rSIFN-co (15 rag), subcutaneous injection, every one day, last 24 weeks. The total cases are 13. After 12 weeks treatment, 7 of 13 (53.85%) were effective. 3 of 13 (23.08%) HBeAg transferred to negative; 7 of 13 (53.85%) HBV-DNA transferred to negative; 11 of 13 (84.62%) hepal functions recovered to normal.

4. The Side Effects of rSIFN-co Compared with IFN-α1b in the Treatment

The side effects of IFN include fever, nausea, myalgia, anorexia, hair lose, leucopenia and thrombocytopenia, etc. The maximum dose of IFN-α1b is 5 MIU per time; the routine dose is 3 MIU. When taken the routine dose, 90% patients have I-II degree (WHO standard) side effects. They are fever lower than 38° C., nausea, myalgia, anorexia, etc. When taken at maximum dose, the rate of side effects do not rise obviously, but are more serious. The maximum dose of rSIFN-co is 24 μg, subcutaneous injection, every one day for 3 months. The routine dose is 9 μg. When routine doses were used, less than 50% patients have I-II degree (WHO standard) side effects, including fever below 38° C., nausea, myalgia, anorexia, leucopenia and thrombocytopenia slightly. With maximum dosage, about 50% patients suffered from leucopenia and thrombocytopenia after using rSIFN-co one month, but those side effects would disappear after stopping treatment for one week. It is safe for continue use.

The Observations of rSIFN-co Treat Hepatitis C

1. Standard of Patient's Selection 1) age: 18-65

2) HCV antibody positive

3) ALT≧1.5 times of the normal value, last more than 6 months

2. Evaluation of the Effects:

Referring to the standard of Infergen® for treatment of hepatitis C and according to the ALT level and HCV-RNA test, divided the effects into three degree:

Response: ALT normal level, HCV-RNA negative

Partial response: ALT normal level, HCV-RNA unchanged

Non response: ALT and HCV-RNA unchanged

3. Effects in Clinic

The clinical trial was done at the same time with hepatitis B treatment. 46 cases received the treatment, 9 μg each time, subcutaneous injection, every day for 24 weeks. After treatment, 26 of 46 (56.52%) have obvious effects, 12 of 46 (26.08%) HCV-RNA transferred to negative, 26 of 46 (56.52%) hepal functions recovered to normal.

---

What is claimed is:

1. A method for treating tumors in a subject, comprising administering to the subject an effective amount of a recombinant interferon which has the amino acid sequence of SEQ ID NO: 2 and is encoded by the nucleotide sequence SEQ ID NO: 1, wherein the tumors are selected from the group consisting of melanoma, renal cell carcinoma, rectal cancer, mammary cancer, ovarian cancer, chronic myelocytic leukemia, hairy cell leukemia, multiple myeloma, Kaposi's sarcoma, non-small cell lung cancer, and small cell lung cancer.

2. The method of claim 1, wherein the tumor is malignant melanoma.

3. The method of claim 1, wherein the tumor is renal cell carcinoma.

4. The method of claim 1, wherein the tumor is rectal cancer.

5. The method of claim 1, wherein the tumor is mammary cancer.

6. The method of claim 1, wherein the tumor is ovarian cancer.

7. The method of claim 1, wherein the tumor is chronic myelocytic leukemia.

8. The method of claim 1, wherein the tumor is hairy cell leukemia.

9. The method of claim 1, wherein the tumor is multiple myeloma.

10. The method of claim 1, wherein the tumor is Kaposi's sarcoma.

11. The method of claim 1, wherein the tumor is small cell lung cancer.

12. The method of claim 1, wherein the tumor is non-small cell lung cancer.

13. The method of claim 1, wherein the interferon is administered via oral, vein injection, muscle injection, peritoneal injection, subcutaneous injection, nasal administration, mucosal administration, or by inhalation via an aspirator.

14. The method of claim 1, wherein the interferon is administered following the protocol of injecting 9 μg or 15 μg per day, 3 times a week, for a total of 24 weeks.

* * * * *

SEQUENCE LISTING

<160> NUMBER OF SEQ ID NOS: 16

<210> SEQ ID NO 1
<211> LENGTH: 504
<212> TYPE: DNA
<213> ORGANISM: Homo sapiens
<220> FEATURE:
<221> NAME/KEY: CDS
<222> LOCATION: (1)..(504)

<400> SEQUENCE: 1

```
atg tgc gac ctg ccg cag acc cac tcc ctg ggt aac cgt cgt gct ctg        48
Met Cys Asp Leu Pro Gln Thr His Ser Leu Gly Asn Arg Arg Ala Leu
1               5                   10                  15 atc ctg ctg gct cag atg cgt cgt atc tcc ccg ttc tcc tgc ctg aaa        96
Ile Leu Leu Ala Gln Met Arg Arg Ile Ser Pro Phe Ser Cys Leu Lys
                20                  25                  30 gac cgt cac gac ttc ggt ttc ccg cag gaa gaa ttc gac ggt aac cag       144
Asp Arg His Asp Phe Gly Phe Pro Gln Glu Glu Phe Asp Gly Asn Gln
            35                  40                  45 ttc cag aaa gct cag gct atc tcc gtt ctg cac gaa atg atc cag cag       192
Phe Gln Lys Ala Gln Ala Ile Ser Val Leu His Glu Met Ile Gln Gln
        50                  55                  60 acc ttc aac ctg ttc tcc acc aaa gac tcc tcc gct gct tgg gac gaa       240
Thr Phe Asn Leu Phe Ser Thr Lys Asp Ser Ser Ala Ala Trp Asp Glu
65                  70                  75                  80 tcc ctg ctg gaa aaa ttc tac acc gaa ctg tac cag cag ctg aac gac       288
Ser Leu Leu Glu Lys Phe Tyr Thr Glu Leu Tyr Gln Gln Leu Asn Asp
                85                  90                  95 ctg gaa gct tgc gtt atc cag gaa gtt ggt gtt gaa gaa acc ccg ctg       336
Leu Glu Ala Cys Val Ile Gln Glu Val Gly Val Glu Glu Thr Pro Leu
            100                 105                 110 atg aac gtt gac tcc atc ctg gct gtt aaa aaa tac ttc cag cgt atc       384
Met Asn Val Asp Ser Ile Leu Ala Val Lys Lys Tyr Phe Gln Arg Ile
        115                 120                 125 acc ctg tac ctg acc gaa aaa aaa tac tcc ccg tgc gct tgg gaa gtt       432
Thr Leu Tyr Leu Thr Glu Lys Lys Tyr Ser Pro Cys Ala Trp Glu Val
    130                 135                 140 gtt cgt gct gaa atc atg cgt tcc ttc tcc ctg tcc acc aac ctg cag       480
Val Arg Ala Glu Ile Met Arg Ser Phe Ser Leu Ser Thr Asn Leu Gln
145                 150                 155                 160 gaa cgt ctg cgt cgt aaa gaa taa                                       504
Glu Arg Leu Arg Arg Lys Glu
                165
```

<210> SEQ ID NO 2
<211> LENGTH: 167

```
<212> TYPE: PRT
<213> ORGANISM: Homo sapiens

<400> SEQUENCE: 2

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Val Asp Ser Ile Leu Ala Val Lys Lys Tyr Phe Gln Arg Ile
        115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165

<210> SEQ ID NO 3
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 3 atg tgt gat tta cct caa act cat tct ctt ggt aac cgt cgc gct ctg      48
Met Cys Asp Leu Pro Gln Thr His Ser Leu Gly Asn Arg Arg Ala Leu
1               5                   10                  15 att ctg ctg gca cag atg cgt cgt att tcc ccg ttt agc tgc ctg aaa      96
Ile Leu Leu Ala Gln Met Arg Arg Ile Ser Pro Phe Ser Cys Leu Lys
            20                  25                  30 gac cgt cac gac ttc ggc ttt ccg caa gaa gag ttc gat ggc aac caa     144
Asp Arg His Asp Phe Gly Phe Pro Gln Glu Glu Phe Asp Gly Asn Gln
        35                  40                  45 ttc cag aaa gct cag gca atc tct gta ctg cac gaa atg atc caa cag     192
Phe Gln Lys Ala Gln Ala Ile Ser Val Leu His Glu Met Ile Gln Gln
    50                  55                  60 acc ttc aac ctg ttt tcc act aaa gac agc tct gct gct tgg gac gaa     240
Thr Phe Asn Leu Phe Ser Thr Lys Asp Ser Ser Ala Ala Trp Asp Glu
65                  70                  75                  80 agc ttg ctg gag aag ttc tac act gaa ctg tat cag cag ctg aac gac     288
Ser Leu Leu Glu Lys Phe Tyr Thr Glu Leu Tyr Gln Gln Leu Asn Asp
                85                  90                  95 ctg gaa gca tgc gta atc cag gaa gtt ggt gta gaa gag act ccg ctg     336
Leu Glu Ala Cys Val Ile Gln Glu Val Gly Val Glu Glu Thr Pro Leu
            100                 105                 110 atg aac gtc gac tct att ctg gca                                     360
Met Asn Val Asp Ser Ile Leu Ala
        115                 120
```

<210> SEQ ID NO 4
<211> LENGTH: 120
<212> TYPE: PRT
<213> ORGANISM: Homo sapiens

<400> SEQUENCE: 4

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Val Asp Ser Ile Leu Ala
        115                 120

<210> SEQ ID NO 5
<211> LENGTH: 108
<212> TYPE: DNA
<213> ORGANISM: Artificial Sequence
<220> FEATURE:
<221> NAME/KEY: CDS
<222> LOCATION: (1)..(108)
<223> OTHER INFORMATION: chemically synthesized

<400> SEQUENCE: 5 atg tgc gac ctg ccg cag acc cac tcc ctg ggt aac cgt cgt gct ctg      48
Met Cys Asp Leu Pro Gln Thr His Ser Leu Gly Asn Arg Arg Ala Leu
1               5                   10                  15 atc ctg ctg gct cag atg cgt cgt atc tcc ccg ttc tcc tgc ctg aaa      96
Ile Leu Leu Ala Gln Met Arg Arg Ile Ser Pro Phe Ser Cys Leu Lys
            20                  25                  30 gac cgt cac gac                                                      108
Asp Arg His Asp
        35

<210> SEQ ID NO 6
<211> LENGTH: 36
<212> TYPE: PRT
<213> ORGANISM: Artificial Sequence
<220> FEATURE:
<223> OTHER INFORMATION: chemically synthesized

<400> SEQUENCE: 6

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp
        35

<210> SEQ ID NO 7
<211> LENGTH: 108
<212> TYPE: DNA

-continued

<213> ORGANISM: Artificial Sequence
<220> FEATURE:
<221> NAME/KEY: Unsure
<222> LOCATION: (1)..(108)
<223> OTHER INFORMATION: chemically synthesized

<400> SEQUENCE: 7
ctgaaagacc gtcacgactt cggtttcccg caggaagaat tcgacggtaa ccagttccag    60
aaagctcagg ctatctccgt tctgcacgaa atgatccagc agaccttc                108

<210> SEQ ID NO 8
<211> LENGTH: 103
<212> TYPE: DNA
<213> ORGANISM: Artificial Sequence
<220> FEATURE:
<221> NAME/KEY: Unsure
<222> LOCATION: (1)..(103)
<223> OTHER INFORMATION: chemically synthesized

<400> SEQUENCE: 8
gctgctggta cagttcggtg tagaattttt ccagcaggga ttcgtcccaa gcagcggagg    60
agtctttggt ggagaacagg ttgaaggtct gctggatcat ttc                     103

<210> SEQ ID NO 9
<211> LENGTH: 103
<212> TYPE: DNA
<213> ORGANISM: Artificial Sequence
<220> FEATURE:
<221> NAME/KEY: Unsure
<222> LOCATION: (1)..(103)
<223> OTHER INFORMATION: chemically synthesized

<400> SEQUENCE: 9
atccctgctg gaaaaattct acaccgaact gtaccagcag ctgaacgacc tggaagcttg    60
cgttatccag gaagttggtg ttgaagaaac cccgctgatg aac                     103

<210> SEQ ID NO 10
<211> LENGTH: 106
<212> TYPE: DNA
<213> ORGANISM: Artificial Sequence
<220> FEATURE:
<221> NAME/KEY: Unsure
<222> LOCATION: (1)..(106)
<223> OTHER INFORMATION: chemically synthesized

<400> SEQUENCE: 10
gaagaaaccc cgctgatgaa cgttgactcc atcctggctg ttaaaaaata cttccagcgt    60
atcaccctgt acctgaccga aaaaaaatac tccccgtgcg cttggg                  106

<210> SEQ ID NO 11
<211> LENGTH: 112
<212> TYPE: DNA
<213> ORGANISM: Artificial Sequence
<220> FEATURE:
<221> NAME/KEY: Unsure
<222> LOCATION: (1)..(112)
<223> OTHER INFORMATION: chemically synthesized

<400> SEQUENCE: 11
ttattcttta cgacgcagac gttcctgcag gttggtggac agggagaagg aacgcatgat    60
ttcagcacga acaacttccc aagcgcacgg ggagtatttt ttttcggtca gg           112

<210> SEQ ID NO 12
<211> LENGTH: 31
<212> TYPE: DNA

```
<213> ORGANISM: Artificial Sequence
<220> FEATURE:
<221> NAME/KEY: Unsure
<222> LOCATION: (1)..(31)
<223> OTHER INFORMATION: chemically synthesized

<400> SEQUENCE: 12
atcggccata tgtgcgacct gccgcagacc c                              31

<210> SEQ ID NO 13
<211> LENGTH: 40
<212> TYPE: DNA
<213> ORGANISM: Artificial Sequence
<220> FEATURE:
<221> NAME/KEY: Unsure
<222> LOCATION: (1)..(40)
<223> OTHER INFORMATION: chemically synthesized

<400> SEQUENCE: 13
actgccaggc tgcagttatt ctttacgacg cagacgttcc                     40

<210> SEQ ID NO 14
<211> LENGTH: 15
<212> TYPE: PRT
<213> ORGANISM: Artificial
<220> FEATURE:
<223> OTHER INFORMATION: Synthetic Construct

<400> SEQUENCE: 6

Cys Asp Leu Pro Gln Thr His Ser Leu Gly Asn Arg Arg Ala Leu
 5                  10                  15

<210> SEQ ID NO 15
<211> LENGTH: 504
<212> TYPE: DNA
<213> ORGANISM: Artificial
<220> FEATURE:
<223> OTHER INFORMATION: chemically synthesized
<220> FEATURE:
<221> NAME/KEY: CDS
<222> LOCATION: (1)..(504)

<400> SEQUENCE: 15
tacacgctgg acggcgtctg ggtgagggac ccattggcag cacgagacta ggacgaccga   60
gtctacgcag catagagggg caagaggacg gactttctgg cagtgctgaa gccaaagggc  120
gtccttctta agctgccatt ggtcaaggtc tttcgagtcc gatagaggca agacgtgctt  180
tactaggtcg tctggaagtt ggacaagagg tggtttctga ggaggcgacg aaccctgctt  240
agggacgacc tttttaagat gtggcttgac atggtcgtcg acttgctgga ccttcgaacg  300
caataggtcc ttcaaccaca acttctttgg ggcgactact tgcaactgag gtaggaccga  360
caatttttta tgaaggtcgc atagtgggac atggactggc ttttttttat gaggggcacg  420
cgaacccttc aacaagcacg actttagtac gcaaggaaga gggacaggtg gttggacgtc  480
cttgcagacg cagcatttct tatt                                        504

<210> SEQ ID NO 16
<211> LENGTH: 360
<212> TYPE: DNA
<213> ORGANISM: Artificial
<220> FEATURE:
<223> OTHER INFORMATION: chemically synthesized
<220> FEATURE:
<221> NAME/KEY: CDS
<222> LOCATION: (1)..(360)

<400> SEQUENCE: 16
```

```
tacacactaa atggagtttg agtaagagaa ccattggcag cgcgagacta agacgaccgt    60
gtctacgcag cataaagggg caaatcgacg gactttctgg cagtgctgaa gccgaaaggc   120
gttcttctca agctaccgtt ggttaaggtc tttcgagtcc gttagagaca tgacgtgctt   180
tactaggttg tctggaagtt ggacaaaagg tgatttctgt cgagacgacg aaccctgctt   240
tcgaacgacc tcttcaagat gtgacttgac atagtcgtcg acttgctgga ccttcgtacg   300
cattaggtcc ttcaaccaca tcttctctga ggcgactact tgcagctgag ataagaccgt   360
```